US012796683B2

(12) United States Patent
Banish et al.

(10) Patent No.: US 12,796,683 B2
(45) Date of Patent: Nov. 17, 2026

(54) DISINFECTANT SYSTEM

(71) Applicant: Michele Banish, Huntsville, AL (US)

(72) Inventors: Michele Banish, Huntsville, AL (US); Richard Banish, Huntsville, AL (US); David Crandall, Huntsville, AL (US)

(73) Assignee: Michele Banish, Huntsville, AL (US)

( * ) Notice: Subject to any disclaimer, the term of this patent is extended or adjusted under 35 U.S.C. 154(b) by 785 days.

(21) Appl. No.: 17/926,736

(22) PCT Filed: May 21, 2021

(86) PCT No.: PCT/US2021/033554
§ 371 (c)(1),
(2) Date: Nov. 21, 2022

(87) PCT Pub. No.: WO2021/237024
PCT Pub. Date: Nov. 25, 2021

(65) Prior Publication Data

US 2023/0276797 A1 Sep. 7, 2023

Related U.S. Application Data

(60) Provisional application No. 63/028,178, filed on May 21, 2020.

(51) Int. Cl.

| | |
|---|---|
| ***A01N 31/08*** | (2006.01) |
| ***A01N 25/02*** | (2006.01) |
| ***A01N 25/18*** | (2006.01) |
| ***A01P 1/00*** | (2006.01) |
| ***A61L 101/34*** | (2006.01) |
| ***C06D 3/00*** | (2006.01) |

(52) U.S. Cl.
CPC ............. *A01N 31/08* (2013.01); *A01N 25/02* (2013.01); *A01N 25/18* (2013.01); *A01P 1/00* (2021.08); *C06D 3/00* (2013.01); *A61L 2101/34* (2020.08)

(58) Field of Classification Search
CPC ........ A01N 31/08; A01N 25/02; A01N 25/18; A01N 65/22; A01N 2300/00; A01P 1/00; C06D 3/00; A61L 2101/34
See application file for complete search history.

(56) References Cited

U.S. PATENT DOCUMENTS

| | | | |
|---|---|---|---|
| 1,886,394 | A | 11/1932 | Goss |
| 2,294,415 | A | 9/1942 | Mcbride |
| 2,482,877 | A | 9/1949 | Louis |
| 2,769,849 | A | 11/1956 | Louis |
| 2,995,526 | A | 8/1961 | De Ment |
| 3,036,939 | A | 5/1962 | Camp |
| 3,625,855 | A | 12/1971 | Douda |
| 3,668,243 | A | 6/1972 | Quinn |
| 3,811,968 | A | 5/1974 | Sayles |
| 3,881,420 | A | 5/1975 | Smith et al. |
| 3,960,087 | A | 6/1976 | Beatty et al. |
| 4,366,010 | A | 12/1982 | Sedat |
| 4,455,252 | A | 6/1984 | Wylegala et al. |
| 4,483,537 | A | 11/1984 | Hanada et al. |
| 4,499,240 | A | 2/1985 | Valentine |
| 4,607,060 | A | 8/1986 | Kmiec et al. |
| 4,692,497 | A | 9/1987 | Gendreau et al. |
| 4,697,521 | A | 10/1987 | Espagnacq et al. |
| 4,841,865 | A | 6/1989 | Liberman |
| 5,098,488 | A | 3/1992 | Hassell et al. |
| 5,154,782 | A | 10/1992 | Shaw et al. |
| 5,340,395 | A | 8/1994 | Larmignat et al. |
| 5,656,794 | A | 8/1997 | Krone et al. |
| 5,679,722 | A | 10/1997 | Tamura |
| 5,744,534 | A | 4/1998 | Ishiharada et al. |
| 6,017,586 | A | 1/2000 | Payn et al. |

(Continued)

FOREIGN PATENT DOCUMENTS

| | | | |
|---|---|---|---|
| CA | 3 056 808 | A1 | 10/2018 |
| CN | 111 011 380 | A | 4/2020 |

(Continued)

OTHER PUBLICATIONS

KR 101535215 B1 machine translation (Year: 2015).*
Li-Mei Dong, Mei Zhang, Qiao-Lin Xu, Qiang Zhang, Bi Luo, Qing-Wen Luo, Wen-Bin Liu and Jian-Wen Tan, "Two New Thymol Derivatives from the Roots of Ageratina adenophora", Molecules, 2017, 22, 592 (Year: 2017).*
Jyoti, Divya Dheer, Davinder Singh, Gulshan Kumar, Manvika Karnatak, Suresh Chandra, Ved Prakash Verma and Ravi Shankar. "Thymol chemistry: A medicinal toolbox." Current Bioactive Compounds 15, No. 5 (2019): 454-474. (Year: 2019).*
"Glycerol propoxylate (1PO/OH) triacryiate—Safety Data Sheet" SIGMA-ALDRiCH Corporation; Version 5.5; revision date May 24, 2016; print date Apr. 26, 2019, pp. 1-7.

(Continued)

*Primary Examiner* — Sue X Liu
*Assistant Examiner* — Nathan W Schlientz
(74) *Attorney, Agent, or Firm* — Nicholas J. Landau; Maynard Nexsen PC

(57) ABSTRACT

A disinfectant method and device produces a disinfectant smoke. The smoke contains reaction products of the initiator compound, sometimes with an additional disinfectant agent. A composition for the non-pyrotechnic generation of the smoke includes a monomer that exothermically polymerizes, an initiator, and a disinfectant agent. A non-pyrotechnic method of generating disinfectant-containing smoke is provided, which includes initiating a frontal polymerization reaction (FPR) in a composition for the non-pyrotechnic generation of disinfectant-containing smoke, and generating disinfectant smoke. A method of disinfecting an area is provided, involving initiating an FPR to generate disinfectant smoke, and exposing the area to the smoke for a period of time sufficient to achieve disinfection. A non-pyrotechnic smoke generator for generating a disinfectant smoke is provided, including the smoke-generating composition comprising and one of either a heat source or a light source positioned to heat or illuminate the composition.

16 Claims, 8 Drawing Sheets

(56) References Cited

U.S. PATENT DOCUMENTS

| | | | | |
|---|---|---|---|---|
| 6,242,521 | B1 | 6/2001 | Hwang | |
| 6,300,457 | B1 | 10/2001 | Rubin et al. | |
| 6,412,416 | B1 | 7/2002 | Rouse et al. | |
| 6,558,487 | B1 | 5/2003 | Tadros | |
| 6,632,839 | B2 * | 10/2003 | Neumann | A01N 37/18 514/627 |
| 6,666,143 | B1 | 12/2003 | Collins | |
| 7,699,004 | B2 | 4/2010 | Muro | |
| 7,946,228 | B2 | 5/2011 | Dindl et al. | |
| 7,975,615 | B1 | 7/2011 | Apple | |
| 9,617,195 | B2 | 4/2017 | Erbach et al. | |
| 10,941,086 | B2 | 3/2021 | Banish et al. | |
| 2001/0018880 | A1 | 9/2001 | Pfeil et al. | |
| 2002/0037960 | A1 | 3/2002 | Kovar et al. | |
| 2002/0132885 | A1 | 9/2002 | Burns et al. | |
| 2003/0114622 | A1 | 6/2003 | Masawaki | |
| 2003/0215588 | A1 | 11/2003 | Yeager et al. | |
| 2006/0147725 | A1 | 7/2006 | Gust et al. | |
| 2008/0199618 | A1 | 8/2008 | Wen et al. | |
| 2009/0155485 | A1 | 6/2009 | Hoyle et al. | |
| 2012/0052281 | A1 | 3/2012 | Ishiguro et al. | |
| 2012/0052881 | A1 | 3/2012 | Heffez | |
| 2012/0055075 | A1 | 3/2012 | Winkler et al. | |
| 2012/0267016 | A1 | 10/2012 | Lombardi | |
| 2013/0172482 | A1 | 7/2013 | Allen et al. | |
| 2014/0020588 | A1 | 1/2014 | Erbach et al. | |
| 2021/0179509 | A1 | 6/2021 | Banish et al. | |

FOREIGN PATENT DOCUMENTS

| | | | | |
|---|---|---|---|---|
| CZ | 8053 | U1 | 1/1999 | |
| DE | 20 2004 021 107 | U1 | 10/2006 | |
| DE | 20 2010 009 717 | U1 | 10/2010 | |
| ES | 2302620 | A1 | 7/2008 | |
| FR | 3 018 277 | A1 | 9/2015 | |
| JP | S59-159809 | A | 9/1984 | |
| JP | 2634849 | B2 | 7/1997 | |
| JP | 2000-07478 | A | 1/2000 | |
| JP | 2000-44691 | A | 2/2000 | |
| JP | 2007-161500 | A | 6/2007 | |
| JP | 2016-069368 | A | 5/2016 | |
| KR | 10-2002-0048605 | A | 6/2002 | |
| KR | 10-2012-0140383 | A | 12/2012 | |
| KR | 101535215 | B1 * | 7/2015 | A01N 65/08 |
| WO | 2006/076033 | A1 | 7/2006 | |
| WO | 2013/169813 | A2 | 11/2013 | |
| WO | 2018/187809 | A1 | 10/2018 | |

OTHER PUBLICATIONS

"US EPA—Pesticides—R.E.D. Fact Sheet for Thymol", Office of Prevention, Pesticides and Toxic Substances, (H-7508W), EPA-738-F-93-010, Sep. 1993, pp. 1-199.

Binici, B., et al., "Spherically Propagating Thermal Polymerization Fronts", Journal of Polymer Science: Part A: Polymer Chemistry, vol. 44, Nov. 20, 2005, pp. 1387-1395.

Capsaicin/C 18H27NO3—PubChem; web-page available at https://pubchern.ncbi.nlrn.nih.gov/cornpound/Capsaicin; pulled from world wide web on Sep. 3, 2019, pp. 1-68.

Charles, Nason et al., "UV Induced Frontal Polymerization of (Meth)Acrylates", © RadTech el5 2004 Technical Proceedings, Apr. 12, 2004, pp. 1-8.

Marini E. et al., "Antimicrobial and Anti-Virulence Activity of Capsaicin Against Erythromycin-Resistant, Cell-Invasive Group A Streptococci", Frontiers in Microbiology, vol. 6, Article 1281, Nov. 13, 2015, pp. 1-7.

Masere, J. et al., "Period-Doubling Behavior in Frontal Polymerization of Multifunctional Acrylates", Choas, vol. 9, Issue 2, 1999, pp. 315-322.

Pojman, J.A., "Frontal Polymerization" In: Matyjaszewski Kand Moller M. (eds), Polymer Science: A Comprehensive Reference, vol. 4, 2012, pp. 957-980.

Pojman, J.A., "Photoinitiated Frontal Polymerization for Rapid Repair and for Studying Sperically Propagating Thermal Fronts", © RadTech el5 2006 Technical Proceedings, Apr. 6, 2006, 8 pages.

Pojman, J.A., et al., "Snell's Law of Refraction Observed in Thermal Frontal Polymerization" Chaos, vol. 17, No. 3, Sep. 1, 2007, 9 pages.

Product Data Sheet. Trigonox 29-408-gr. 1, 1-Di(tert-butylperoxy)-3,3,5-trimethyl cyclohexane granules 40% on calcium carbonate and silica. AkzoNobel. Apr. 2010, 2 pages.

Scoville, W.L., "Note on Capsicums", The Journal of the American Pharmaceutical Association, vol. 1, 1912, pp. 453-454.

V.G. Viner et al., "The effect of phase change materials on the frontal polymerization of a triacrylate," Physica D, vol. 239, 2010, pp. 838-847.

Washington, R.P., et al., "Frontal Free-Radical Polymerization: Applications to Materials Synthesis", Polymer News 2003, Copyright © 2003 Taylor & Francis, Inc., vol. 28, No. 10, 2003, pp. 303-310.

Xia, W.Z. et al., "Exotherm control in the thermal polymerization of nona-ethylene glycol dimethacrylate (NEGDM) using a dual radical initiator system", Polymer 44, Copyright © 2002 Published by Elsevier Science Ltd, vol. 44, No. 1, Nov. 22, 2002, pp. 79-88.

International Search Report and Written Opinion issued Dec. 16, 2013, in International Patent Application No. PCT/US2013/03994, filed May 7, 2013, 14 pages.

Extended European Search Report and Opinion mailed on Dec. 1, 2015, in European Patent Application No. 13788459.9, filed on May 7, 2013, 11 pages.

Office Action mailed on Aug. 22, 2016, in European Patent Application No. 13788459.9, filed on May 7, 2013, 3 pages.

International Search Report and Written Opinion mailed on Jul. 26, 2018, in International Patent Application No. PCT/US2021/033554, mailed on Sep. 22, 2021, 14 pages.

International Preliminary Report on Patentability received for International Patent Application No. PCT/US2021/033554, mailed on Dec. 1, 2022, 9 pages.

International Search Report and Written Opinion mailed on Jul. 26, 2018, in International Patent Application No. PCT/US2018/026731, filed on Apr. 9, 2018, 8 pages.

International Preliminary Report on Patentability received for International Patent Application No. PCT/US2013/039994, mailed on Nov. 20, 2014, 11 pages.

International Search Report and Written Opinion mailed on Jul. 26, 2018, in International Patent Application No. PCT/US2013/039994, mailed on Dec. 16, 2013, 20 pages.

Examination Report No. 1 mailed on May 11, 2021, in Australian Patent Application No. 2018249955, filed on Apr. 9, 2018, 2 pages.

International Preliminary Report on Patentability received for International Patent Application No. PCT/US2018/026731, mailed on Oct. 17, 2019, 7 pages.

Cheng, S-Y. et al., "Runaway reaction on tert-butyl peroxybenzoate by DSC tests", Journal of Thermal Analysis and Calorimetry, Kluwer Academic Publishers NL, vol. 93, Issue 1, Jul. 1, 2008, pp. 121-126 (Abstract only).

Tseng, J-M et al., "Evaluation of a tert-Butyl Peroxybenzoate Runaway Reaction by Five Kinetic Models", Industrial and Engineering Chemistry Research, American Chemical Society, vol. 50, No. 8, Apr. 20, 2011, pp. 4783-4787 (Abstract only).

Viner V., et al., "Effect of Filler Choice on a Binary Frontal Polymerization System", Journal of Physical Chemistry B, American Chemical Society, vol. 115, No. 21, Jun. 2, 2011, pp. 6862-6867 (Abstract only).

Viner V., et al., "Effects of thiols, lithium chloride, and ethoxylated monomers on the frontal polymerization of a triacrylate", Journal of Polymer Science, Part A: Polymer Chemistry, John Wiley and Sons Inc., vol. 49, No. 21, Nov. 1, 2011, pp. 4556-4561 (Abstract only).

* cited by examiner

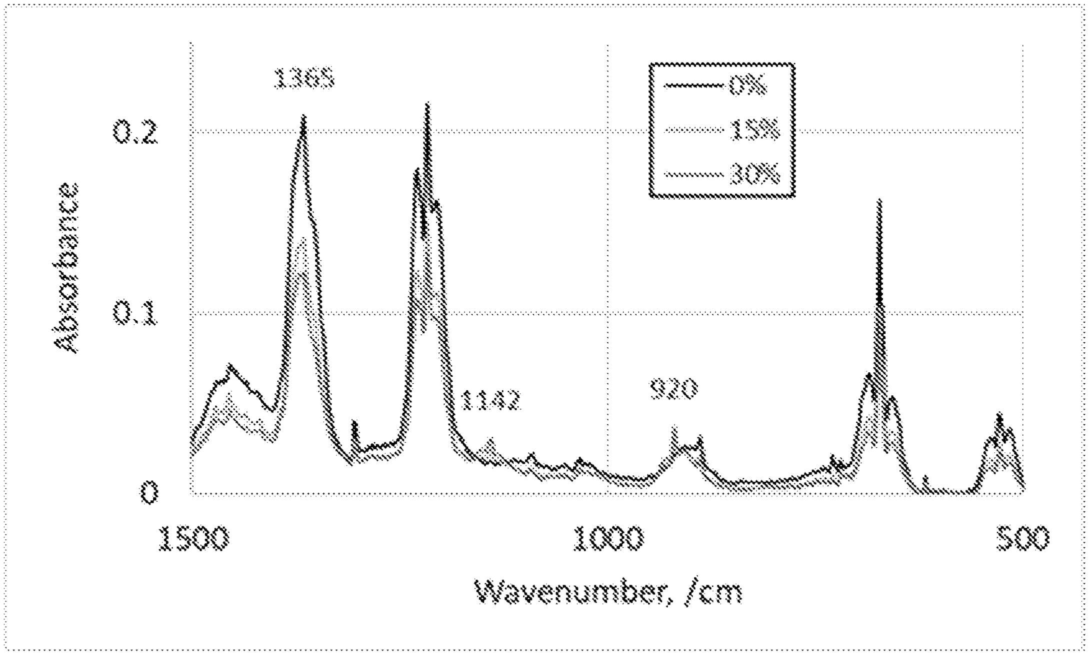
FIG. 13A
FIG. 13B
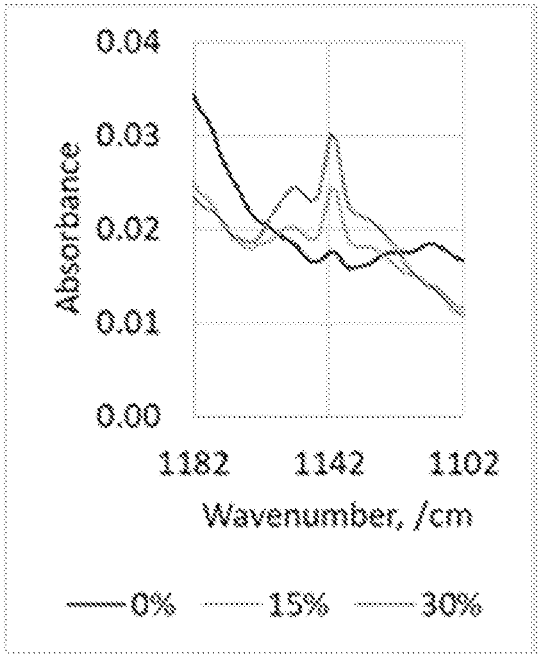
FIG. 13C
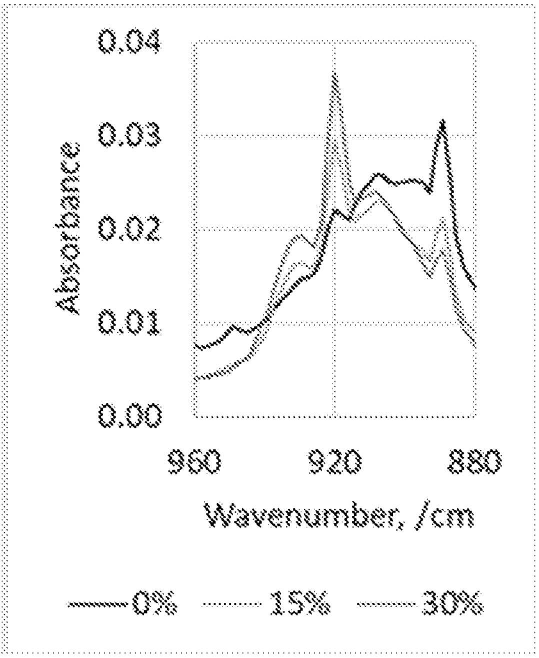

DISINFECTANT SYSTEM

CROSS-REFERENCE TO RELATED APPLICATIONS

This is a national stage application under 35 U.S.C. 371 of International Application PCT/US2021/033554, filed on 21 May 2021. International Application PCT/US2021/033554 cites the priority under 35 U.S.C. 119 of 63/028,178, filed on 21 May 2020. The contents of each of the foregoing are incorporated herein by reference in their entireties.

STATEMENT OF FEDERAL FUNDING

This invention was made with government support under the Department of Defense grant number W81XWH22C0010. The government has certain rights in the invention. In this context "government" refers to the government of the United States of America.

BACKGROUND

The disinfection of surfaces and airspaces is critical to the maintenance of public health, yet there are few working systems that can disinfect large areas quickly and efficiently. Ultraviolet radiation is sometimes used for this purpose (and lower wavelengths of electromagnetic radiation as well), but it has serious drawbacks. Ultraviolet radiation cannot infiltrate all porous surfaces. Ultraviolet lights cast shadows that create safe zones for infectious agents. Ultraviolet light is hazardous with which to work, requiring protective equipment be used during the disinfection process. It can also damage materials, particularly plastics. Ducts, vents, and the like cannot be disinfected using ultraviolet radiation unless the lamp is inserted into the duct or vent.

Airborne disinfectants are another approach. Airborne disinfectants will penetrate porous objects, can flow around obstructions such as furniture, can flow through small spaces, can be designed to persist for prolonged periods, and can be formulated to be harmless to materials. Airborne delivery systems include smokes, fogs, and sprays. Sprays have the disadvantage of low airborne residence times as compared to smokes and fogs, seriously limiting their utility.

Devices for producing smoke either rely on combustion or explosion (collectively "pyrotechnics"). Combustive smoke generation devices burn an organic fuel with or without an inorganic oxidizer. Examples of these smoke generation devices are thermite grenades, HC (hexachloroethane), TA (terephthalic acid), and WP (white phosphorus, or red phosphorus) smoke grenades. The reactions in these devices have large free energies of reaction, and are by necessity highly exothermic. As such, the reactions produce dangerous levels of heat; many also produce smoke that is toxic or otherwise hazardous. The adiabatic flame temperatures of these materials greatly exceed 1000° C., which is one of the factors that leads to their incendiary characteristics. Such heat levels can set cloth, fuel, ammunition and other combustibles on fire. Exposure of persons to them can cause fatal burns, and inhalation of the hot and/or toxic smoke can also be fatal.

Explosives have the same drawbacks as combustive systems in that they generate very high temperatures and often the smoke is toxic. Explosives can also cause injury and property damage due to shrapnel and concussion. Explosives have not been found to be useful for disinfectant dispersal.

Fog generators operate at lower temperatures by vaporizing a liquid fog solution (commonly an aqueous glycol solution). The fog solution is evaporated in heated air, then blown out through a fan. When the warm and moist air from the fog generator contacts the cooler ambient air, it causes the vaporized solution to form a fog. These devices are generally safer than pyrotechnic smoke generators. However, fog generators are bulky, require a large volume of fog solution to be on hand, and require large amounts of energy (in the form of electricity) to vaporize the fog solution and to operate the fan. As a result, they are poorly suited for work in the field and are not very portable.

Consequently, there is a need in the art for a portable means to deliver disinfectant agents in the form of a smoke or fog, ideally a non-toxic and non-pyrotechnic smoke or fog that will neither poison nor burn those exposed to it.

SUMMARY

It has been found that some disinfectant agents can be aerially dispersed in smoke that is generated non-pyrotechnically (without flame or explosion) through a frontal polymerization reaction (FPR). The FPR generates a small amount of heat that causes a component of the composition to form a fog or a smoke (referred to herein generally as a "smoke" for the sake of simplicity). Because the smoke is formed at relatively low temperature, the smoke can contain additives with low flashpoints, or that thermally degrade at lower temperatures, that would be destroyed by pyrotechnic methods.

It has further been found that the addition of "excess" initiator increases the amount of smoke and decreases the quality of the resultant polymer. Generally during polymerization, the greater the concentration of initiator the poorer the strength of the resultant polymer, due to voids, fractures, and other defects. Without wishing to be bound to any hypothetical model, it is believed that increasing the initiator concentration beyond the minimum necessary to sustain the polymerization reaction causes an excessive number of polymerization reactions to occur simultaneously; resulting in shorter polymer chains and in a far weaker polymer product. As the initiator concentration is increased excessively, the polymer product has much shorter chains and is far weaker. Although a disadvantage if one wishes to produce good quality polymer, this can be an advantage in the production of disinfectant smoke.

In a first aspect, a composition for the non-pyrotechnic generation of disinfectant-containing smoke is provided, the composition comprising: a monomer that exothermically polymerizes upon initiation with an initiator to generate a smoke; the initiator that initiates polymerization of the monomer, said initiator present at a mass concentration that is at least one tenth the mass concentration of the monomer; and a disinfectant agent.

In a second aspect, a non-pyrotechnic method of generating disinfectant-containing smoke is provided, the method comprising initiating an FPR in a composition for the non-pyrotechnic generation of disinfectant-containing smoke, and generating smoke comprising the disinfectant agent.

In a third aspect a smoke is provided that is the product of a non-pyrotechnic method of generating disinfectant-containing smoke is provided, the method comprising initiating an FPR in a composition for the non-pyrotechnic generation of disinfectant-containing smoke, and generating smoke comprising the disinfectant agent.

In a fourth aspect a disinfectant-containing smoke is provided, the smoke comprising: a disinfectant agent and a reaction product of an initiator.

In a fifth aspect a method of disinfecting an area is provided, comprising: generating a disinfectant containing smoke by initiating an FPR in a composition for the non-pyrotechnic generation of disinfectant-containing smoke; generating smoke comprising the disinfectant agent; and exposing the area to the smoke for a period of time sufficient to achieve disinfection.

In a sixth aspect, a non-pyrotechnic smoke generator for generating a disinfectant-containing smoke is provided, said smoke generator comprising: a support member having a length and a width; a composition supported by the support member comprising a monomer that exothermically polymerizes upon initiation with an initiator to generate a smoke, the initiator that initiates polymerization of the monomer present at a mass concentration that is at least the mass concentration of the monomer, and a disinfectant agent; and one of either a heat source or a light source positioned to heat or illuminate the composition.

In a seventh aspect, a method of disinfecting an area is provided, comprising: generating a disinfectant smoke by initiating an FPR in a composition comprising a monomer that exothermically polymerizes upon initiation with an initiator to generate a smoke and the initiator that initiates polymerization of the monomer; and exposing the area to the smoke for a period of time sufficient to achieve disinfection.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

FIG. 13 depicts the FTIR spectrum of Luperox P produced mist along with dissolved thymol for several different thymol concentrations: A shows the spectrum at 1500-500 $cm^{-1}$, B shows the spectrum at 1182-1102 $cm^{-1}$, and C shows the spectrum at 960-880 $cm^{-1}$.

DETAILED DESCRIPTION

Figure 1:
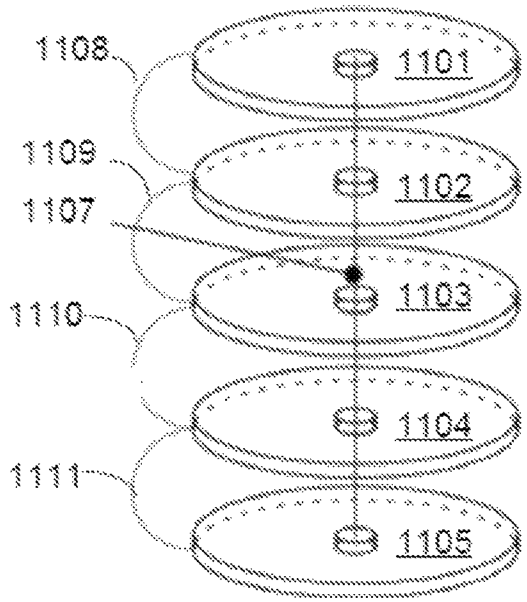
FIG. 1 depicts a "stacked disc" embodiment of a smoke generating device.

The disclosure provides compositions, methods, and devices for producing smoke or fog containing one or more disinfectant agents. It is not entirely clear whether the compositions disclosed produce airborne suspensions of liquid droplets (fog) or solid particles (smoke), but for the sake of brevity the term "smoke" is used to refer to the airborne suspension. In any instance where the term "smoke appears" it should be interpreted to include a smoke or a fog (or even a mixed smoke and fog).

Various embodiments of the compositions disclosed herein may have one or more advantages over previously known smoke-producing compositions; for example: low or no flame is produced (safe to use indoors, outdoors, and in training environments with flame hazards); low toxicity of the smoke and any non-smoke residues; environmentally friendly (little to no residue or hazardous byproducts); high packing density; high smoke yield/low agglomeration of smoke particles; easily aerosolized; rapid smoke generation (short time constant); good obscuration properties in the visible portion of the electromagnetic spectrum; long smoke durations with appropriate buoyancy; and good shelf life (i.e., after mixing components, the mixture does not self-initiate and/or self-polymerize).

The disinfectant smoke is created not through combustion or explosion, but by an FPR. Frontal polymerization is a process in which a polymerization reaction propagates directionally through a reaction mass because of the coupling of thermal transport and the Arrhenius-dependence of the kinetics of an exothermic reaction. In FPRs, the components are premixed, but stable until initiated by an external source. This is unlike other systems, such as a 2-part epoxy: as soon as the two components are mixed, an exothermic reaction is initiated. As another example, RTV type polymers will self-initiate once exposed to oxygen. The reactions developed here operate differently than either of these or similar types of examples.

FPR is a form of self-propagating high-temperature synthesis (SPHTS). Here the term "high-temperature" is used to indicate higher than ambient temperature, but certainly lower in temperature than pyrotechnic smoke generation. In FPR as in the case of SPHTS the system will not start reacting until sufficient energy is applied to the material to get a reaction front propagating through the system. This self-propagating wave moves rapidly through the system so long as sufficient heat is generated at the propagation front. Thus, these systems are inherently stable until enough energy is added to start the reaction. Materials with high heat capacity can be incorporated into the mixture to moderate the reaction. Thus, the system can be tuned such that the heat released does not lead to excessive heating (or burning) of the surrounding environment, thereby reducing incendiary hazards. For example, the addition of filler materials has the effect of reducing the front temperature and thereby reducing the incendiary hazard by diluting the concentration of monomer and initiator and by raising the specific heat of the composition.

I. Definitions

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred when not expressly stated.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Terms such as "at least one of A and B" should be understood to mean "only A, only B, or both A and B." The same construction should be applied to longer lists (e.g., "at least one of A, B, and C").

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

In some places reference is made to standard methods, such as but not limited to methods of measurement. It is to be understood that such standards are revised from time to time, and unless explicitly stated otherwise reference to such standard in this disclosure must be interpreted to refer to the most recent published standard as of the time of filing.

II. Compositions that Generate Disinfectant Smoke

In a general embodiment, the composition comprises a monomer that exothermically polymerizes upon initiation with an initiator to generate a smoke, the initiator itself present at a mass concentration that is at least one tenth the mass concentration of the monomer, and a disinfectant agent in an amount effective to produce a disinfectant effect in the smoke.

Without wishing to be bound by any hypothetical model, it is believed that the smoke is mainly reaction products of the initiator. These reaction products are believed to be one or both of thermal decomposition products and oligomerization products. It is further believed that the exothermic polymerization of the monomer generates sufficient heat to volatilize the reaction products of the initiator. It is also believed that the disinfectant is dissolved in the smoke particles, although it is possible that some amount of disinfectant is volatilized during smoke generation.

Since the initiator is the source of the smoke in this embodiment, it is only necessary to have a sufficient reaction temperature to sustain the initiator decomposition/oligomerization reaction and maintain the FPR. Conventional smoke generation involves the combustion of a fuel (often with an oxidizer) that vaporizes a separate component that forms the smoke. Since the smoke created by polymerization of embodiments of the present smoke generating composition is composed of reaction products of the initiator itself, an additional component is not strictly necessary (although it may be included in some embodiments). Without wishing to be bound by any hypothetical model, it is believed that the monomer itself may also decompose or oligomerize to form part of the smoke in some embodiments.

In some embodiments of the composition, the reactants have reaction temperatures in the range of up to 300° C. Various embodiments of the composition contain reactants that create smoke under conditions that differ significantly from pyrotechnic methods. For example, the reactants may react to create smoke wherein the reaction is flameless, nonexplosive, requires no $O_2$, consumes no $O_2$, and any combination of two or more of the foregoing. In a specific embodiment of the composition, $O_2$ is not a reactant in the exothermic reaction. Furthermore, other oxidants might not be required. Oxidants that are used in pyrotechnic applications include inorganic and organic forms of chlorate, perchlorate, nitrate, sulfate, permanganate, and chromate; and inorganic forms of peroxide and oxide. Commonly used cations include sodium, potassium, barium, ammonium, strontium, lead, cesium, bismuth, iron, and manganese. Some embodiments of the composition lack any significant amount of one or more inorganic oxidizers. The "significant amount" can mean no more than 10% w/w. Some embodiments of the composition contain no more than 10%, 9%, 8%, 7%, 6%, 5%, 4%, 3%, 2%, 1%, 0.5% and 0.1% w/w of a chlorate, perchlorate, nitrate, sulfate, permanganate, chromate, an inorganic peroxide, and an inorganic oxide. A specific embodiment of the composition contains none of a chlorate, perchlorate, nitrate, sulfate, permanganate, chromate, an inorganic peroxide, and an inorganic oxide.

In experimental testing of the smoke producing composition of the present disclosure, it was found that increasing the amount of initiator in the compound increased the amount of smoke produced. The composition may have a w/w ratio of initiator:monomer of at least 5% (i.e., 5 g of initiator per 95 g of monomer). Various embodiments of the composition may have higher w/w ratios of initiator:monomer, such as at least 1:10, 1:5, 1:2, 3:5, 7:10, 3:4, 4:5, 85:100, 95:100, 99:100, 1:1, 2:1, 3:1, 4:1, 5:1, 6:1, 7:1, 8:1, 9:1, 10:1, 15:1, 20:1, and a range between any two of the foregoing. In a specific embodiment the initiator:monomer mass ratio is in the range of 5:1-20:1.

Without wishing to be bound by any hypothetical model, it is believed that the monomer provides heat (through exothermic polymerization) to vaporize the smoke components. It is also possible that the degradation of the initiator contributes heat during the FPR that vaporizes the smoke components. The monomer may be one that is suitable to participate in an FPR, such as a trifunctional monomer, having three double-bond carbon ends associated with each monomer molecule. Some preferred embodiments of the composition contain a triacrylate monomer. Specific examples of triacrylate monomers potentially suitable in the composition are trimethylolpropane triacrylate (TMPTA), glycerol propoxylate (1-PO/OH) triacrylate (GPOTA), and trimethylpropane propoxylate triacrylate (TMP(PO)TA). Combinations of such monomers could potentially be used as well. Note that the monomer may also be a material with a backbone other than carbon; for example, the silicon backbone in silicone caulk or RTV sealant. In addition, the production of a polymer is not a strict necessity, so long as an exothermic polymerization reaction occurs.

Some embodiments of the composition contain an additional component that forms the smoke. Components such as methyl benzoate, benzyl benzoate, and pentyl acetate, also increase smoke production but reduce buoyancy. These materials are esters used as food additives and have the advantage of low toxicity.

The initiator functions to initiate the polymerization of the monomer when sufficient energy is introduced. One suitable class of initiators is organic peroxides. Specific examples of organic peroxide initiators include di-tert-butyl peroxide, tert-butyl peroxybenzoate, tert-butyl hydroperoxide, and cyclohexyl hydroperoxide. The composition may contain one or more of the foregoing, alone or in combination.

The specific heat and/or concentration of monomer and initiator can be modulated by the addition of a “filler.” The filler does not participate in the FPR, and may be a generally unreactive compound. Suitable fillers include fumed silica, kaolin powder, powdered sugar, and any combination of two or more of the foregoing. Fumed silica has the advantages that the mass required is low and a high area-mass ratio which provides significant thickening with a low thermal mass. The filler should be present at a concentration sufficient to achieve propagation of the FPR at a controlled rate-preventing the monomer from polymerizing too quickly (producing excessive heat) while allowing the production of sufficient heat for polymerization. For example, some embodiments of the composition contain at least 2% w/w filler. Further embodiments contain at least 5% w/w filler. More specific embodiments of the composition contain 5-20% w/w filler. A specific embodiment of the composition contains 5-20% w/w fumed silica.

The combination of the monomer, initiator, filler, and other components will contribute to the initiation temperature, when thermal initiation is used. The “initiation temperature” is the temperature to which the composition must be raised locally (in one particular area) in order to start the FPR, when thermal initiation is used. In some embodiments of the composition, the initiation temperature is no more than 200° C. In some embodiments of the composition, the initiation temperature is no more than 160° C. In further embodiments of the composition, the initiation temperature is no more than 130° C. In more specific embodiments of the composition, the initiation temperature is 100-160° C. In further specific embodiments of the composition, the initiation temperature is 120-130° C. These initiation temperatures have the advantage of being well below the flash points of many common construction materials, meaning that thermal initiation can be achieved without the use of a dangerously hot heat source. In alternative embodiments photoinitiation is used by directing a light source of sufficient intensity to trigger initiation on the composition.

The combination of the monomer, initiator, filler, and other components will contribute to the temperature the composition reaches during the FPR and/or during the generation of the smoke. Some embodiments of the composition will not exceed a given maximum temperature during the FPR and/or during the generation of the smoke. In some such embodiments, the composition does not exceed 300° C. during the FPR and/or during the generation of the smoke.

An infrared-opaque agent may be included in the composition to increase the opacity of the smoke in the IR spectrum. Ideally the IR-opaque agent will be at least partially soluble in the composition and will migrate into the smoke. Some suitable embodiments of the IR-opaque agent are: methyl benzoate, benzyl benzoate, pentyl acetate, and any combination of two or of the same. Infrared-opaque smoke has the advantage of allowing the smoke to be monitored using IR sensors.

Some embodiments of the composition are translucent or transparent over at least a portion of the infrared spectrum. This has the advantage of preventing the smoke from obscuring the use of IR cameras. Some embodiments of the composition generate smoke that is translucent or transparent over at least a portion of the infrared spectrum that includes $\lambda$=1.4 μm.

The composition can be formulated in various physical states. These states include a solid, a liquid, and a suspension (among others). Some embodiments of the composition are not fluid. Such non-fluids may include a solid and a semi-solid. Exemplary semi-solids include a gel, colloid, slurry, paste, and slime. Fluid forms include a liquid. A non-fluid form has the advantage of preventing or reducing convection during the FPL, and may be formed to allow more controlled propagation of a frontal polymerization reaction.

Non-fluid embodiments of the composition may be manufactured with a defined shape. For example, a sheet is especially useful if an FPR is desired. Suitable sheets may be created as strips, discs, spirals, tapes, and other shapes in which the first dimension (e.g., height) is much smaller than at least one of the other two dimensions. Such flat shapes allow the formation of a reaction front that spreads along only one or two axes. Another example is a paste applied in a line.

Fluid embodiments of the composition could potentially be used by dispensing a controlled amount to an initiation mechanism to produce smoke at a controlled rate.

An initiation mechanism may be present in the composition. The initiation mechanism provides sufficient energy to initiate polymerization, in form of heat, electromagnetic radiation, or other forms. Some embodiments of the initiation mechanism are a heat source. The heat source may be a non-pyrogenic heat source. Embodiments of the non-pyrogenic heat source may be a conductive wire connected to a source of electric current, a heated gas, a source of electromagnetic radiation, a solid heat conductor, a nichrome wire loop connected to an electric power source, a heat gun, a soldering iron, focused light, a piezoelectric device, and a combination of the foregoing. One exemplary embodiment of the initiation device is a 1" conduction loop of 30 gauge (0.01") nickel-chromium (NiCr, or nichrome) wire with a resistance/unit length of approximately 4.5 Ohm/in. Testing has shown that a current draw of approximately 1 Amp is sufficient to initiate the FPR is some embodiments of the composition. Using Power, $P=I^2R$, where I is the current in Amps and R is the resistance in Ohms, this yields an input Power of $P=(1\ \text{Amp})^2(4.5\ \text{Ohm})=4.5$ W.

The addition of a filter can be useful in compositions in which the primary mixture components of the smoke producing composition have enough thermal conductivity that, if a point ignition source is applied, the bulk mixture reactants may quickly convect the required reaction energy away from the reaction site and cause the reaction to quench itself. The very low thermal conductivity of fumed silica "insulates" the reaction region, preventing the heat of reaction or of initiation from convecting away too rapidly. When no filler is present a large area heat source, such as a heat gun, may be required to inject significant heat into the mixture to overwhelm the convective heat losses. Present experimentation has shown cases where, for all other mixture components held constant, increases in filler (fumed silica) have resulted in a higher absorption smoke. The filler may provide more nucleation sites for polymerization/oligomerization to initiate.

A preferred embodiment of the composition comprises glycerol propoxylate triacrylate (as the monomer), tert-peroxybenzoate (as the initiator) present at a mass concentration that is 5-20 times the mass concentration of the monomer, and thymol as the disinfectant.

The disinfectant should be present in an amount sufficient to exert a disinfectant effect. A disinfectant effect exists if at least 50% of infectious agents are killed or inactivated. In some embodiments the disinfectant effect is a kill or inactivation rate of at least 50%, 80%, 85%, 90%, 95%, 99%, 99.9%, 99.99%, 99.999%, or 99.9999%. The infectious agent may include a bacterium, a virus, a fungus, and a combination of two or more of the foregoing. Examples of the infectious agent may include one or more of *Staphylococcus, Staphylococcus aureus, Staphylococcus aureus* (ATCC 6538), methicillin resistant *Staphylococcus aureus, Staphylococcus aureus*-HA-MRSA (ATCC 33591), a coronavirus, a human coronavirus, SARS-CoV-2, SARS-CoV-2 ATCC VR-740 Strain 229E, *Enterobacter, E. aerogenes, Enterobacter aerogenes* (ATCC 13048), *Candida albicans, Escherichia coli, Salmonella enterica*, influenza A (H1N1), *Pseudomonas aeruginosa*, rhinovirus type 37, and mildew.

The disinfectant effect can be measured by any of several methods, such as surface disinfection tests. Specific examples that may be used to determine the disinfectant effect of the smoke include: ASTM E1053-20, "Standard Practice to Assess Virucidal Activity of Chemicals Intended for Disinfection of Inanimate, Nonporous Environmental Surfaces;" ASTM E1153-14 "Standard Test Method for Efficacy of Sanitizers Recommended for Inanimate, Hard, Nonporous Non-Food Contact Surfaces;" ASTM E2721-16 "Standard Practice for Evaluation of Effectiveness of Decontamination Procedures for Surfaces When Challenged with Droplets Containing Human Pathogenic Viruses;" ASTM E3031-15 "Standard Test Method for Determination of Antibacterial Activity on Ceramic Surfaces;" ASTM E3218-19 "Standard Test Method for Quantitative Method for Testing Antimicrobial Agents against Spores of *C. difficile* on Hard, Nonporous Surfaces;" ASTM E2720-16 "Standard Practice for Evaluation of Effectiveness of Decontamination Procedures for Air-Permeable Materials when Challenged with Biological Aerosols Containing Human Pathogenic Viruses." In a specific embodiment of the method, a disinfectant effect shall mean an effect that kills or inactivates at least 50% of viruses according to ASTM E1053-20. In addition, the disinfectant effect may be measured by the method taught in the examples below to measure virucidal activity and antibacterial activity. Unless specified otherwise, a disinfectant effect shall mean an effect that kills or inactivates at least 50% of bacteria or viruses according to one of the methods taught in the examples below.

The disinfectant will ideally dissolve in the smoke generating composition and segregate into the smoke fraction during smoke generation. Without wishing to be bound by any given hypothetical model, it is believed that alcohols and organic acids have adequate disinfectant properties, will dissolve in embodiments of the smoke generating composition, and will at least partially segregate into the smoke fraction.

In some embodiments of the composition the disinfectant is an active ingredient of a disinfectant on the list of registered disinfectants publicly maintained by the United States Environmental Protection Agency. In further embodiments of the composition is an active ingredient of a disinfectant on List A, List B, List C, List D, List E, List F, List G, List H, List I, List J, List K, List L, List M, and List N. In a specific embodiment the disinfectant is an active ingredient of a disinfectant product from List N, for example thymol. In some cases, the disinfectant may be one that was included in any of the foregoing lists as of the filing date of this application. Some embodiments of the composition comprises one or more of the following disinfectants: thyme oil, a thymol compound, thymol (2-isopropyl-5-methylphenol), thymyl-4-nitrobenzoate, a thymyl salt, a thymyl ester, a citrate compound, citric acid, a citrate salt, a citrate ester, a caprylate compound, caprylic acid, a caprylate salt, a caprylate ester, a lactate compound, lactic acid, L-lactic acid, a lactate salt, and a lactate ester.

In further embodiments of the composition the disinfectant is a thymol compound selected from the following:

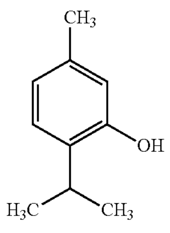

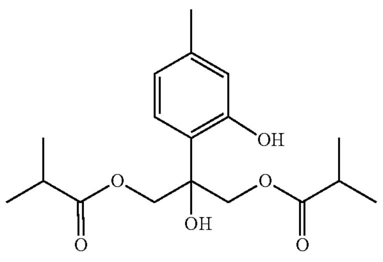

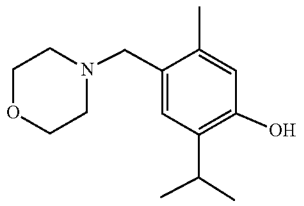

-continued
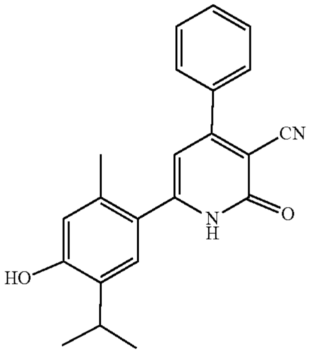
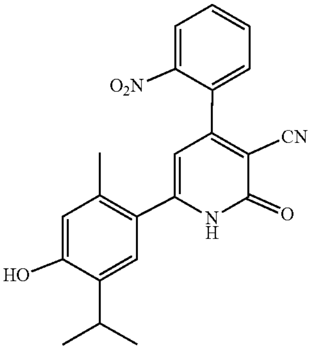
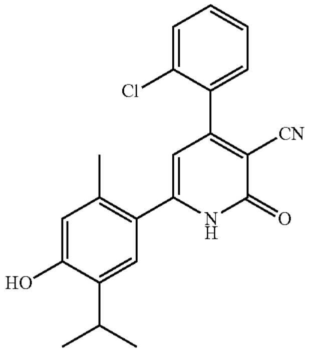
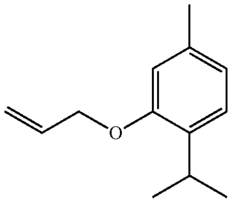
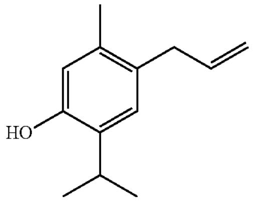
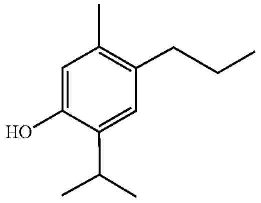
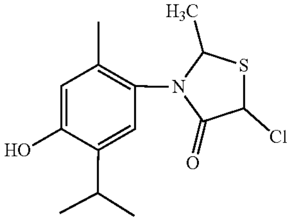
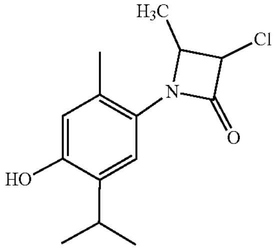
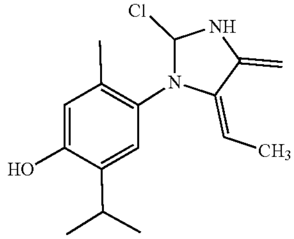
-continued
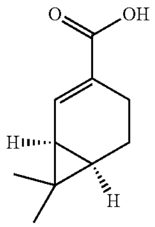
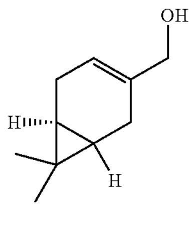
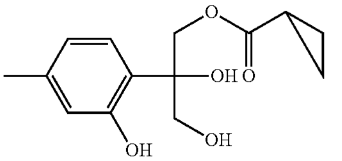
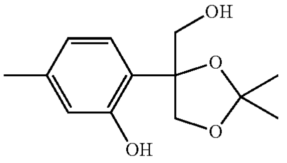
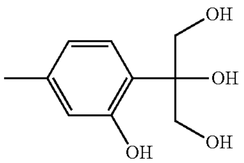
28
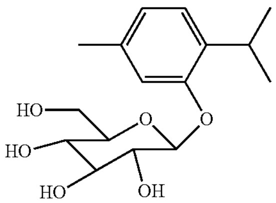
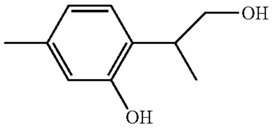
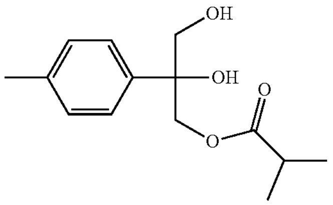
31
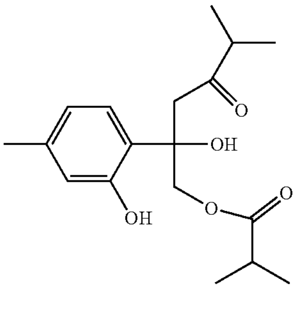
32
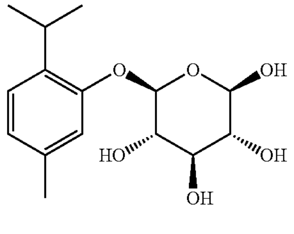

-continued
41
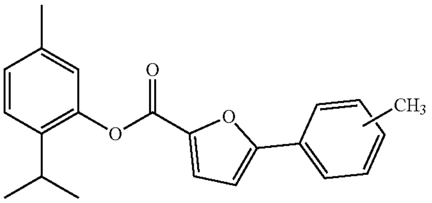
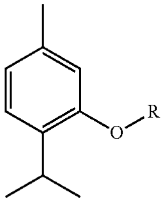
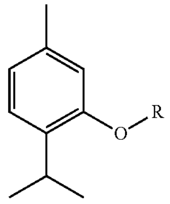
42. = $CH_3$-$CH_2$-CH2-
43. = $C_6H_5$-$CH_2$-
44. R = $CH_3$-
45. R = $C_6H_5$-
46. R = $(CH_3)_2CH$-
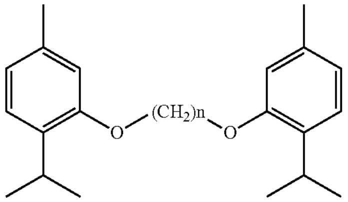
47. n = 1
48. n = 2
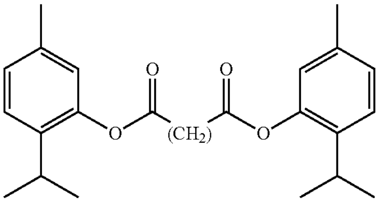
49
50
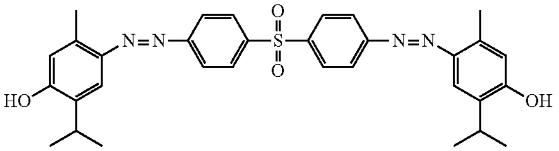
77
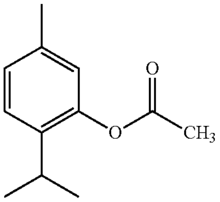
78
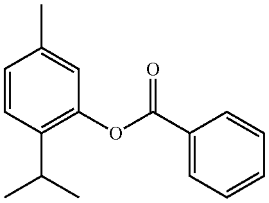
-continued
79
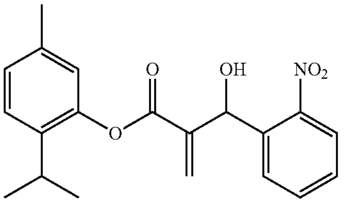
80
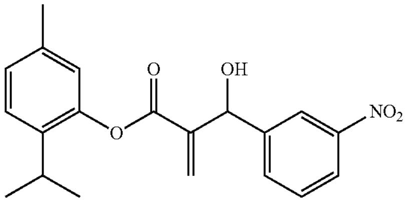
81
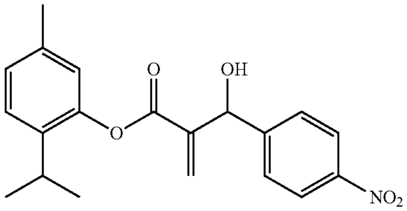
82
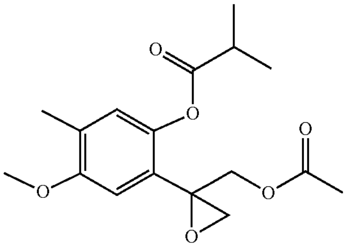
83
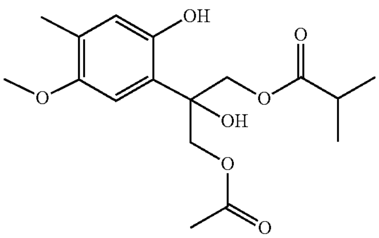
84
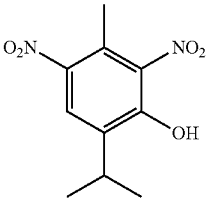
85
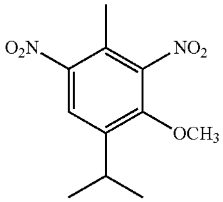

-continued

86

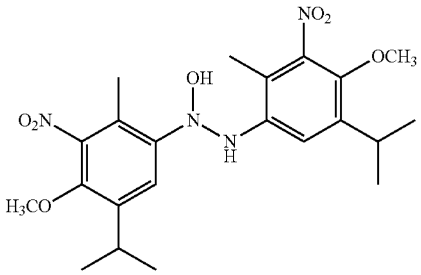

87

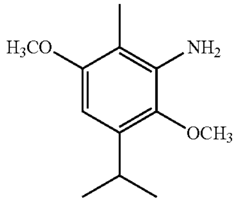

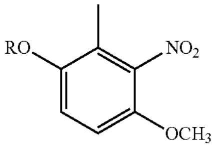

88. R—CH3
89. R—H

90

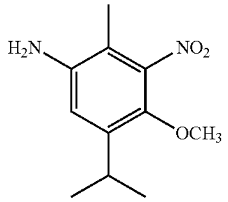

91

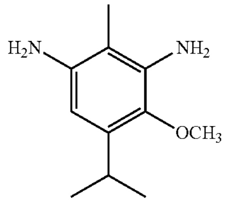

The concentration of the disinfectant in the smoke is affected by the relative concentrations of the disinfectant and the initiator. Some embodiments of the composition comprise the disinfectant at a mass concentration at least 50% of the mass concentration of the initiator. In further embodiments of the composition the disinfectant is present at a mass concentration at least 1%, 2%, 3%, 4%, 5%, 6%, 7%, 8%, 9%, 10%, 15%, 20%, 25%, 30%, 35%, 40%, 45%, 50%, 60%, 70%, 80%, 85%, 90%, 95%, 99%, and 100% of the mass concentration of the initiator. In a further embodiment of the method the disinfectant is present at no more than 10%, 15%, 20%, 25%, 30%, 35%, 40%, 45%, 50%, 60%, 70%, 80%, 85%, 90%, 95%, 99%, and 100% of the mass concentration of the initiator. In some embodiments of the method the disinfectant is present at no more than 15%, 16%, 17%, 18%, 19%, 20%, 25%, 30%, 35%, 40%, 45%, 50%, 60%, 70%, 80%, 85%, 90%, 95%, 99%, and 100% of the mass concentration of the initiator.

III. Methods of Generating and Using Disinfectant Smoke

A non-pyrotechnic method of generating disinfectant-containing smoke is provided, comprising initiating a frontal polymerization reaction in a composition for the non-pyrotechnic generation of disinfectant-containing smoke, and generating smoke comprising the disinfectant agent. The composition may be any of the smoke-generating compositions disclosed above. Because the smoke is generated by an FPR, in at least some embodiments of the method the smoke is not produced by combustion. Furthermore, in at least some embodiments of the method the smoke is generated non-explosively. It is preferred that the method involves the non-pyrotechnic generation of the disinfectant smoke, involving neither flame nor explosion. As discussed above, such embodiments may have the advantage of generating the smoke without $O_2$ being a reactant in the smoke generating reaction. In some embodiments of the method no inorganic oxidizer is a reactant in the smoke generating reaction. Consequently, in such embodiments of the method $O_2$ is not consumed while smoke is generated.

It has also been observed that smoke generated from an FRP between the monomer and initiator has disinfectant properties in the absence of a separate disinfectant agent, although in some cases the addition of a disinfectant agent increases the disinfectant activity of the smoke. In such embodiments no separate disinfectant agent need be present in the composition for the smoke itself to have disinfectant properties. For the purposes of this disclosure the "disinfectant agent" is not a reaction product of the monomer and initiator.

Without wishing to be bound by any hypothetical model, it is believed that the method generates smoke that mainly comprises (at least 50% w/w) the disinfectant and reaction products of the initiator and. Some embodiments of the method will generate smoke that is at least 1%, 2%, 3%, 4%, 5%, 6%, 7%, 8%, 9%, 10%, 15%, 20%, 25%, 30%, 35%, 40%, 45%, 50%, 75%, 80%, 85%, 90%, 95%, or 100% reaction products of the initiator and the disinfectant. In a further embodiment of the method the disinfectant is present at no more than 10%, 15%, 20%, 25%, 30%, 35%, 40%, 45%, 50%, 60%, 70%, 80%, 85%, 90%, 95%, 99%, and 100% of the mass concentration of the initiator.

The method comprises initiating the FPR. If thermal initiation is used the initiating step comprises heating the composition of any one of the claims above to an initiation temperature suitable to initiate polymerization of the monomer with the initiator. This heating must be localized if an FPR is desired, as heating the entire composition to the initiation temperature would result in the entire composition polymerizing simultaneously. The localized heating can be at a point, along a line, over a relatively small region, or using a similar approach. Some embodiments of the method have the advantage of requiring relatively low temperatures for thermal initiation. In some such embodiments initiation can be accomplished by locally heating the composition to a temperature of no more than about 200° C. In further such embodiments the initiation is accomplished by heating the composition to a temperature of 100-200° C. In still further embodiments the initiation is accomplished by heating the composition to a temperature of 100-160° C. In still further embodiments the initiation is accomplished by heating the composition to a temperature of no more than about 130° C.

Thermal initiation can be accomplished using any of various heaters. For example, thermal initiation could be accomplished by running an electric current through an electrically conductive material in contact with the composition. In a preferred embodiment the conductive material is a nickel-chromium wire. The power source can be as simple as a 9 V battery. The heat source can also be a thermally conductive material in contact with the composition, where the thermally conductive material is in contact with a heater.

Some embodiments of the method have the advantage of producing disinfectant smoke at low temperatures. In some embodiments of the method the composition does not exceed 300° C. during the generation of the smoke. In some such embodiment the smoke itself may not exceed 300° C.

The smoke finds use in a method of disinfection. The smoke as generated by any of the methods described above may be exposed to one or more surfaces to be disinfected. Exposure should be conducted for a period of time sufficient to achieve the desired disinfectant effect. The subject of disinfection can be a volume of air, a surface, a workpiece, an organism, a garment, a vehicle, a building, and the like. The level of disinfection can be any described above as meeting the definition of a "disinfectant effect." For example, the level of disinfection may be measured by ASTM E2721-16 "Standard Practice for Evaluation of Effectiveness of Decontamination Procedures for Surfaces When Challenged with Droplets Containing Human Pathogenic Viruses." Organisms can be disinfected by virtue of the low toxicity of the smoke and the low temperature of the smoke when a disinfectant of low toxicity is also used. Types of organisms that can be disinfected include crop plants, humans, livestock, and other animals. Disinfection would be expected to be effective at least on the organism's external surfaces.

IV. Disinfectant Smoke

A disinfectant-containing smoke is provided. As described above, the smoke comprises a reaction product of an initiator that participated in a polymerization reaction, and a disinfectant agent. As discussed above, it is believed that the smoke comprises reaction products of the initiator, such as thermal decomposition products and initiator oligomerization products. More specific embodiments of the smoke comprise a reaction product of an initiator from an FPR. The initiator from which the reaction product is derived may be any described above as suitable in the composition.

The smoke may be produced by any of the methods described above.

The smoke will in some cases be opaque in the visible spectrum, although this is not critical so long as the disinfectant is effectively dispersed in the smoke. However, visual opacity has the advantage of allowing the dispersal of the smoke to be easily monitored. The smoke may also be opaque in the infrared spectrum, which has the advantage of allowing the dispersal of the smoke to be monitored using infrared sensors. Alternatively, the smoke may be non-opaque in at least part of the infrared spectrum, to allow IR cameras and sensors to function unhindered during its use. In a specific embodiment the smoke is non-opaque over at least part of the infrared spectrum that includes $\lambda$=1.4 μm; this is a wavelength at which many infrared cameras are sensitive. If infrared opacity is desired, the smoke may comprise an infrared-opaque agent, such as any listed above as suitable for use in the composition.

V. Disinfection Devices

Figure 10:
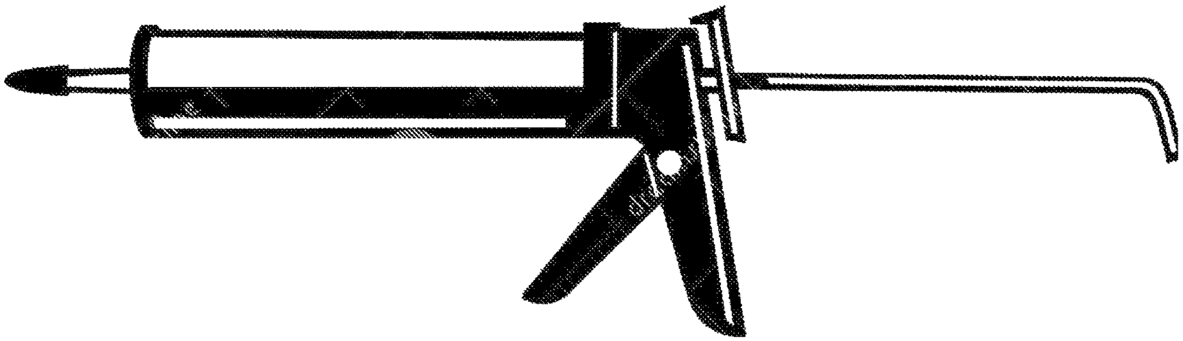
FIG. 10 depicts an embodiment of a caulk gun that could be used to dispense a bead or line of composition for generating disinfectant-containing smoke.

The composition finds use in a non-pyrotechnic disinfectant device that generates a disinfectant-containing smoke. A general embodiment of the device comprises a support member having a length and a width; the composition of any one of the claims above supported by the support member; and a heat source positioned to heat the composition. An alternative general embodiment of the device is a caulk dispenser loaded with any of the compositions disclosed above (FIG. 10); in such embodiments a line of the composition can be deposited on a surface, and the FPL can be initiated anywhere along the line.

Figure 11:
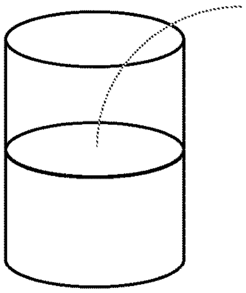
FIG. 11 depicts an embodiment of a cannister that could be used to distribute the disinfectant smoke.

An alternative general embodiment of the device is a cup at least partially filled with disinfectant smoke composition (FIG. 11). Such embodiments may comprise a volume of any one of the disinfectant-containing smoke generating compositions in the claims above in the cup, and a heating device to initiate an FPL in said composition. The heating device may take any suitable form, as described below.

An alternative general embodiment of the device is a plug-in wall unit. Such general embodiments may comprise a plug to connect to a power source, a heating device powered by said power source, and a volume of any one of the disinfectant-containing smoke generating compositions in the claims above positioned to be initiated by the heating device.

The heat source can advantageously be non-pyrotechnic, such as a source of electric current, a heated gas, a solid heat conductor, or a radiation source. Some embodiments of the device may use a pyrotechnic heat source to trigger the otherwise non-pyrotechnic reaction. Examples of pyrotechnic heat sources include a fuse. In a specific embodiment the heat source is a wire in contact with the composition and connected to a source of electric current. In a further specific embodiment, the heat source is a nickel-chromium wire connected to a source of electric current. The heat source may be configured to limit the temperatures generated into a relatively safe range. In some such embodiments of the device heat source is configured to generate a temperature of no more than about 200° C. In further such embodiments of the device the heat source is configured to generate a temperature of 100-200° C. In still further such embodiments of the device the heat source is configured to generate a temperature of 100-160° C. In a specific embodiment of the device the heat source is configured to generate a temperature of no more than about 160° C. In a further specific embodiment of the device the heat source is configured to generate a temperature of no more than about 130° C.

The support member may be dimensioned to modulate the duration of the FPR of the composition. One way this can be accomplished is by providing a support member that is longer in one dimension than another (i.e. the ratio of the length to the width is more than about 1:1). Because an FPR generally spreads in all directions at about the same rate, the support member becomes more efficient in terms of duration of the FPR per unit mass when it is longer and thinner. Various examples of such configuration include: a support member that is a spiral and in which the ignition wire contacts the spiral at the center of the spiral or the edge; a support member that is a coiled strip and in which the ignition wire contacts the support member at the center of the coil or the edge of the coil; multiple support members each being a coiled strip, and in which the ignition wire contacts each of the said support members at the center of the coil or the edge of the coil; multiple support members each having the shape of an arc of an open cylinder, and contacting the other support members along a line of contact from the top to the bottom of the cylinder, wherein the ignition wire runs along the line of contact.

Other shapes of the support member can be used to modulate smoke production as needed. For example, when the support member is a disc and the ignition wire contacts the center of the disc, smoke will be produced at an accelerating rate as the front of the FPR expands as a circle of increasing circumference.

The support member functions to hold the smoke generating composition and provide it with shape. In a specific embodiment the support member comprises a fibrous matrix onto which the composition is deposited (e.g., coated). In some such embodiments the smoke generating composition occupies a significant portion (at least 25% v/v) of the interstices in the matrix. In further embodiments the composition may occupy more specific portions of the interstitial volume of the matrix, for example at least 30, 35, 40, 45, 50, 55, 60, 65, 70, 75, 80, 85, 90, 95, 99, or 100% v/v. The matrix itself may comprise fibers of various compositions, such as polymer fibers, natural fibers, metallic fibers, and ceramic fibers. The matrix could also comprise one or more wires that serve as the heat source ("ignition wires," although nothing is ignited).

Figure 12:
FIG. 12 depicts an embodiment of a drone aircraft that could be used to distribute the disinfectant smoke.

Some embodiments of the disinfectant device take the form of other more conventional smoke generators, such as a grenade, a handheld grenade, a rifle grenade, a 40 mm grenade, and a 66 mm vehicle-launched grenade. In a specific embodiment of the disinfectant device the composition is carried by a remotely controlled vehicle or a robot vehicle (FIG. 12). Such vehicles may non-exclusively include an aircraft, a watercraft (surface vessel or submersible), a wheeled vehicle, a tracked vehicle, a hovercraft, and a ground-effect vehicle.

VI. EXAMPLES

Some of the below examples are working examples, in which terms such as "we" and "our" appear in reference to those involved in the work. Terms such as "we," "our," and "our group" used below refer to persons who contributed to the work and the writeup thereof, some of whom might not be considered "inventors" of what is claimed under the laws of certain countries; the use of such terms is neither a representation nor an admission that any person is legally an inventor of what is claimed.

Example 1: Disinfectant Smoke Generator

FIG. 1 depicts an embodiment of a smoke generating device 1100 using the composition disclosed herein. In this "stacked disk arrangement," an embodiment of the smoke generating compound (not shown) is applied to disks 1101, 1102, 1103, 1104 and 1105 stacked atop one another. Although five (5) disks 1101-1105 are shown in FIG. 1, this number of disks is illustrated for explanatory purposes; a smoke generating device 1100 may comprise 10-30 stacked disks, or more or fewer, as desired.

In this embodiment, each disk 1101-1105 is formed from non-woven fiber, such as a plastic fiber similar to Scotch Brite® pads or a plastic Brillo® pad, or fiberglass. The disks 1101-1105 may also be formed from other materials with a high surface area for maximizing the composition's exposure to oxygen during the smoke-producing reaction.

An ignition wire 1106 extends through openings 1107 in the disks 1101-1105 for initiating the reaction. In other embodiments, the ignition wire 1106 may be "woven" into the fiber comprising the disk.

Wires 1108, 1109, 1110, and 1111 extend between adjacent disks. In this regard, wire 1108 extends between disk 1101 and disk 1102; wire 1109 extends between disk 1102 and disk 1103; wire 1110 extends between disk 1103 and disk 1104; wire 1111 extends between disk 1104 and disk 1105.

In some embodiments, insulators (not shown) are disposed between adjacent disks to isolate each disk from the remaining disks, to prevent the disks from sticking together.

Figure 2:
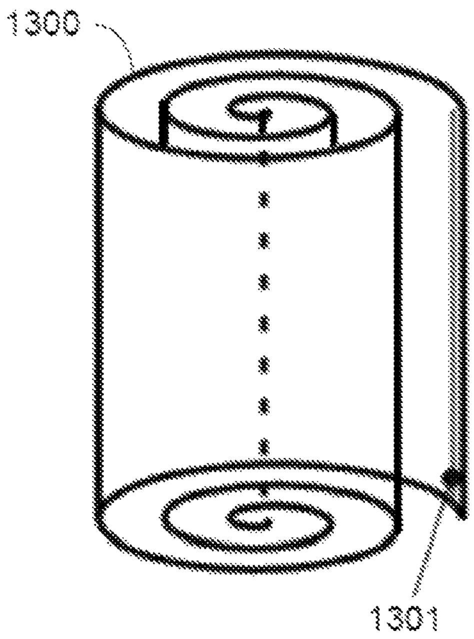
FIG. 2 depicts an embodiment of a smoke producing device comprising a substrate formed from a single sheet of material, rolled into a spiral shape.

FIG. 2 depicts an embodiment of a smoke producing device comprising a substrate 1300 formed from a single sheet of material, rolled into a spiral shape as shown. The substrate 1300 may be formed from the materials discussed above with respect to FIG. 1. An ignition line 1301 extends through the substrate 1300.

Figure 3:
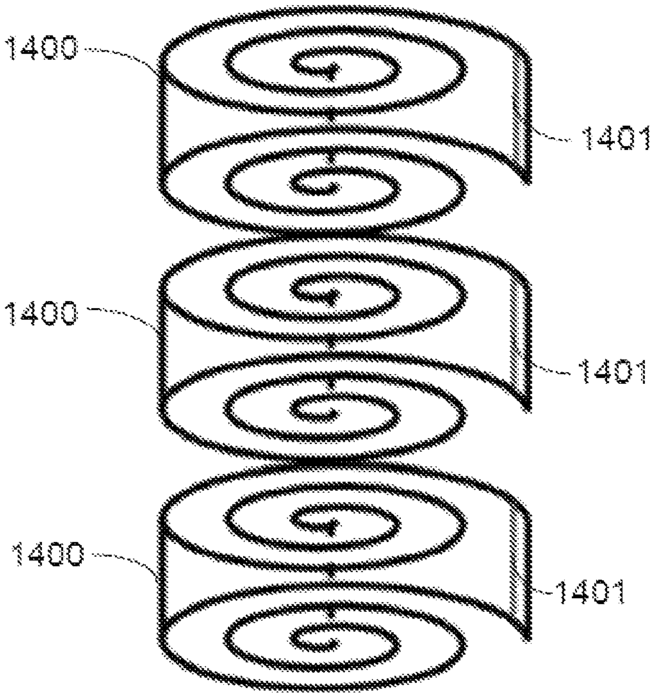
FIG. 3 depicts a "stacked spiral" arrangement in which a plurality of spiral substrates stacked atop one another.

FIG. 3 depicts a "stacked spiral" arrangement in which a plurality of spiral substrates 1400 like those discussed above with respect to FIG. 2 are stacked atop one another. Each substrate comprises an ignition line 1401.

Figure 4A:
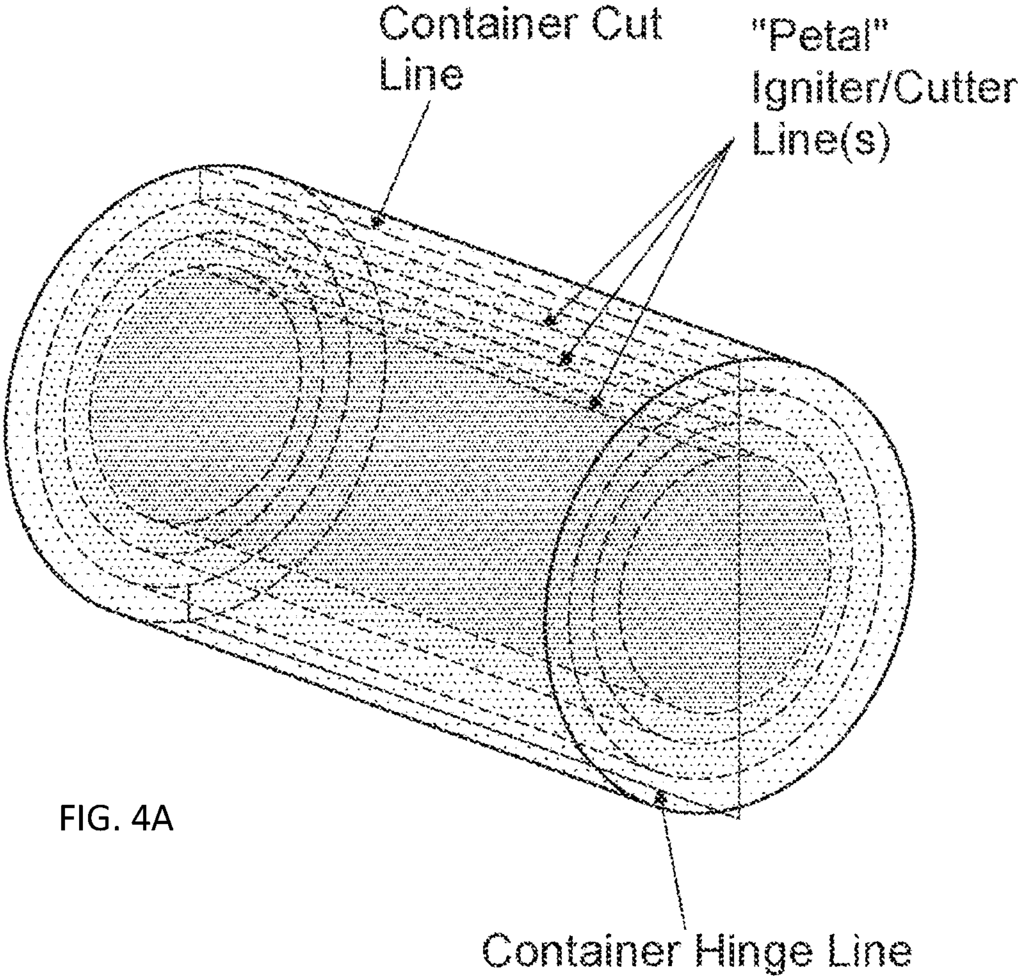
FIGS. 4A, 4B and 4C depict an embodiment of a smoke producing device in which a plurality of cylindrical petals are arranged "concentrically" inside a cylindrical container that is hinged on one side.
Figure 4B:
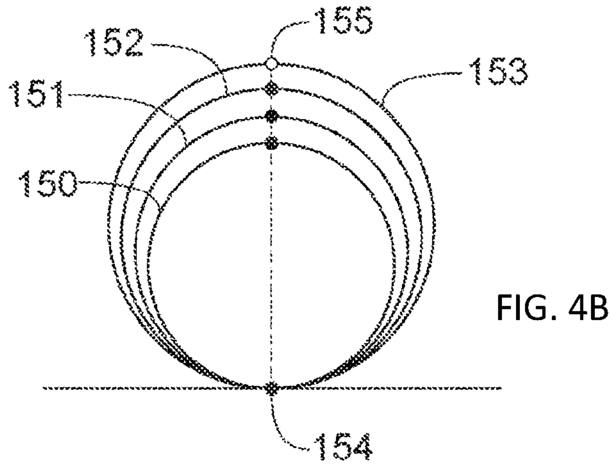
Figure 4C:
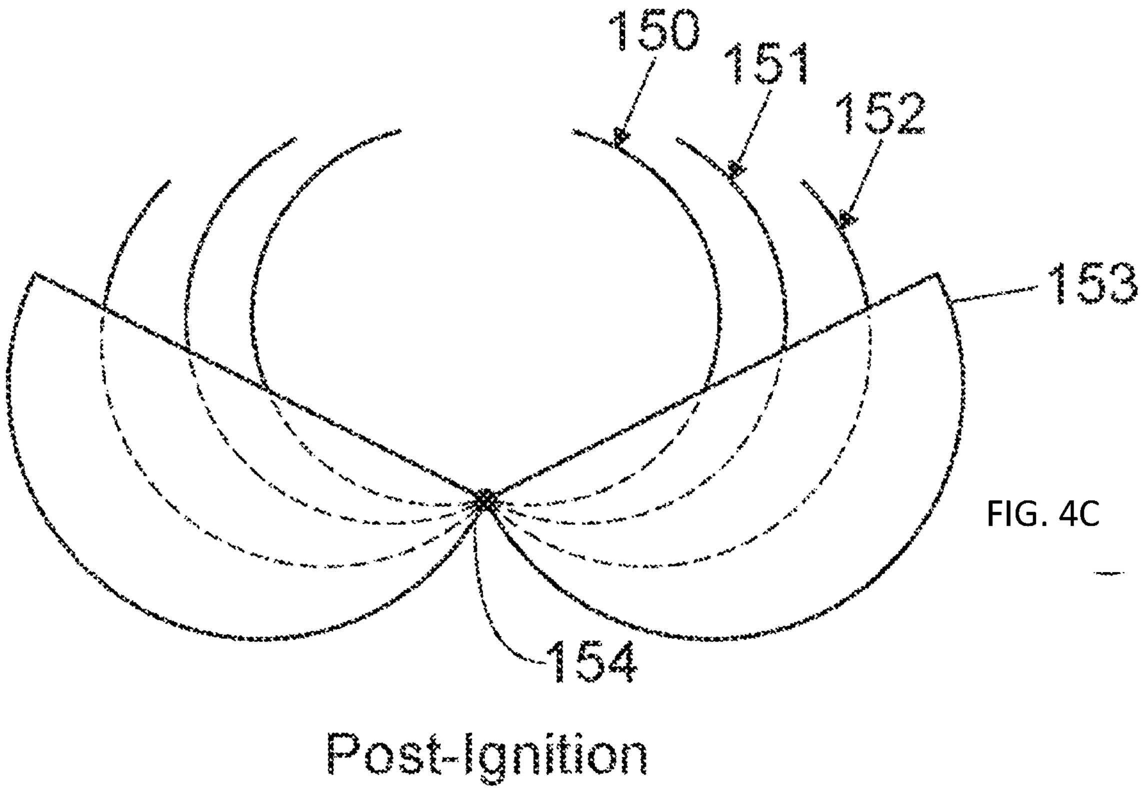

FIGS. 4A, 4B and 4C depict an embodiment of a smoke producing device in which a plurality of cylindrical petals 150, 151 and 152 nested inside a cylindrical container 153 that is hinged on one side via a hinge 154. FIGS. 4A and 4B depict the container 153 before the smoke producing ignition is initiated, and FIG. 4C depicts the container 153 after the ignition has begun. Although three petals 150, 151, and 152 are depicted in the illustrated embodiment, more or fewer petals are employed in other embodiments.

The ignition sequence causes the container 153 to be split so that it opens up along a hinge line 155 of the container 153. The concentrically arranged petals 150, 151 and 152 are ignited and split along one side so that they "open up" like a blooming flower. Each of the petals 150, 151 and 152 may be formed from the materials discussed with respect to FIG. 1 above.

Example 2: Disinfectant Testing

Three disinfectants were tested: benzyldimethylhexadecylammonium chloride, citric acid, and thymol.

Solubility in an embodiment of the smoke generating composition, comprising Luperox P, TMPTA, fumed silica, and an organic disinfectant (benzyldimethylhexadecylammonium chloride, thymol, or citric acid) was tested. A 50% thymol/Luperox P (5 g thymol for each 10 g Luperox P (t-butyl peroxybenzoate)) solution was achieved. Neither benzyldimethylhexadecylammonium nor citric acid dissolved.

Figure 5:
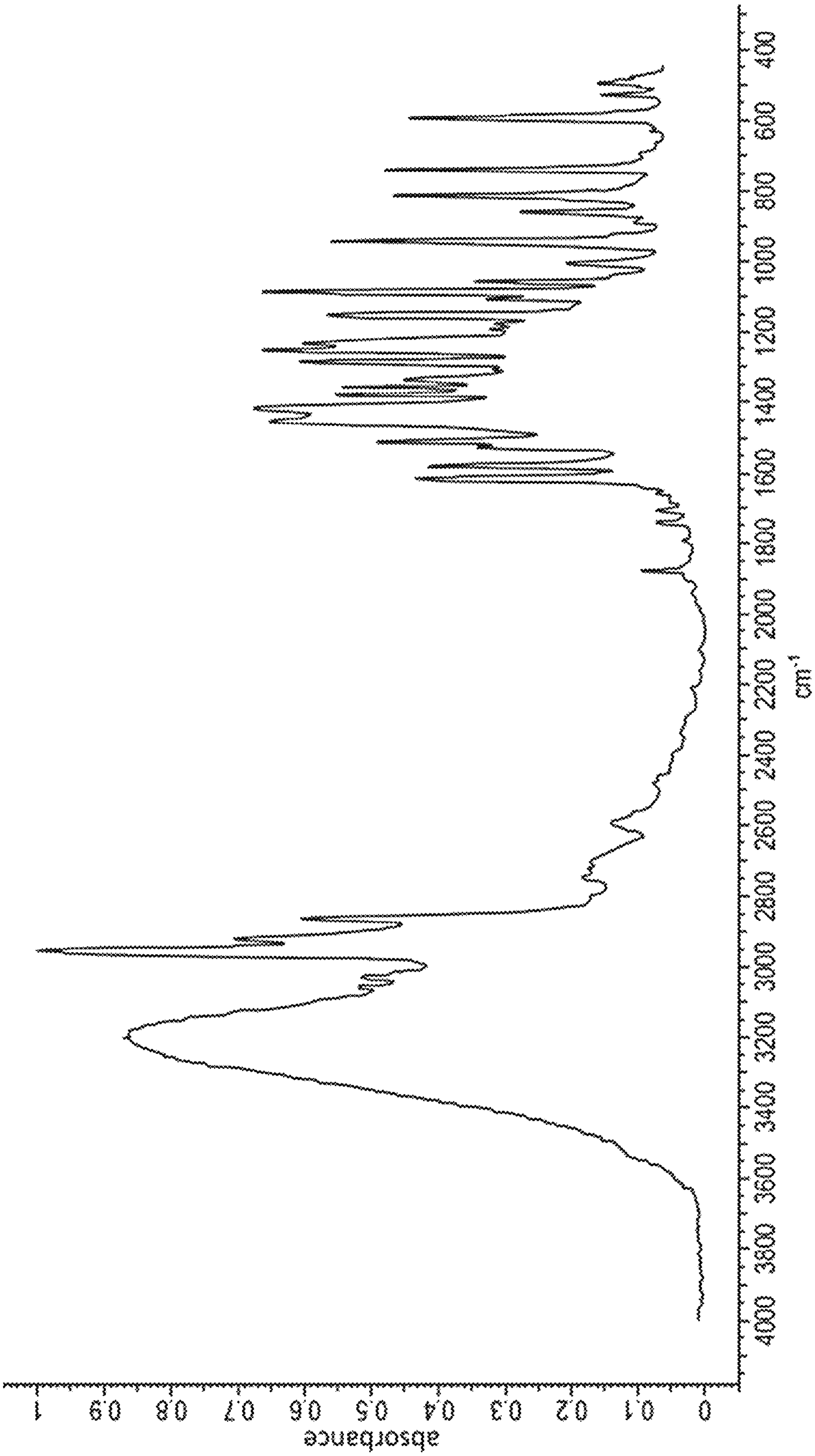
FIG. 5 (PRIOR ART)
FIG. 5 is an absorbance spectrum of an embodiment of the smoke generating composition and the resulting smoke, with and without the disinfectant thymol.

Thymol was dispersed in the carrier fluid of initiator and monomer by dissolution in Luperox P followed by the addition of TMPTA monomer. The fluid without thymol was also tested for a baseline. A sample was placed in a chamber and then "smoked". A KBr IR card was placed in the smoke path to collect condensable product. The exposed cards were then read by Fourier-transform infrared spectroscopy for spectral signatures. The absorbance spectrum of thymol alone is shown in FIG. 5.

Figure 6:
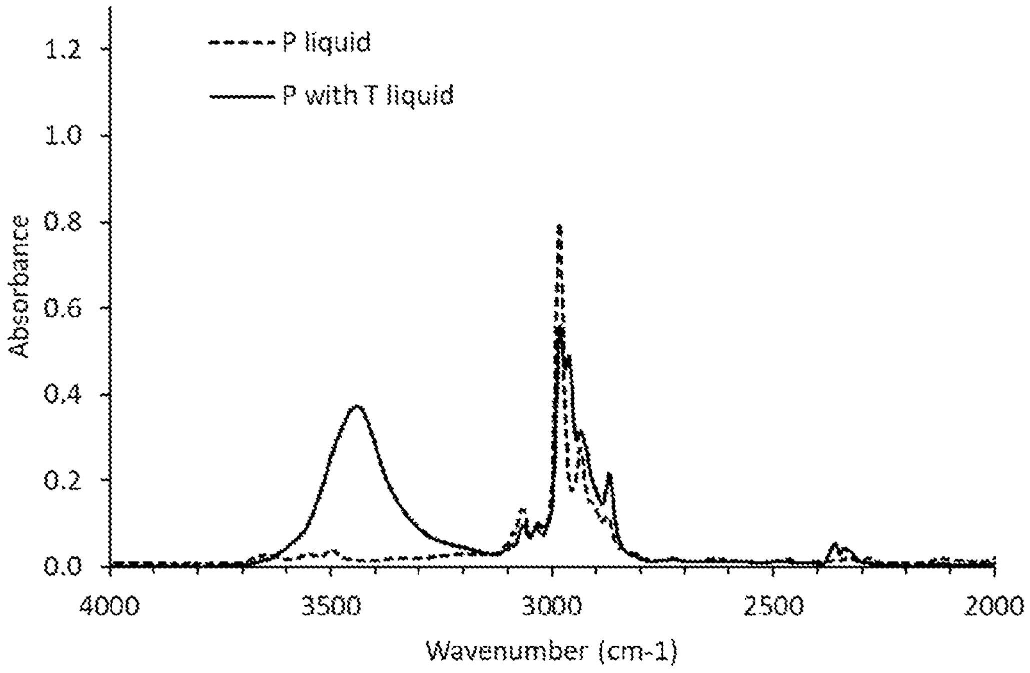
FIG. 6 is an absorbance spectrum of an embodiment of the disinfectant-containing composition as compared to the same composition without disinfectant, in which the disinfectant is thymol, and over the range of 2000-4000 $cm^{-1}$.
Figure 7:
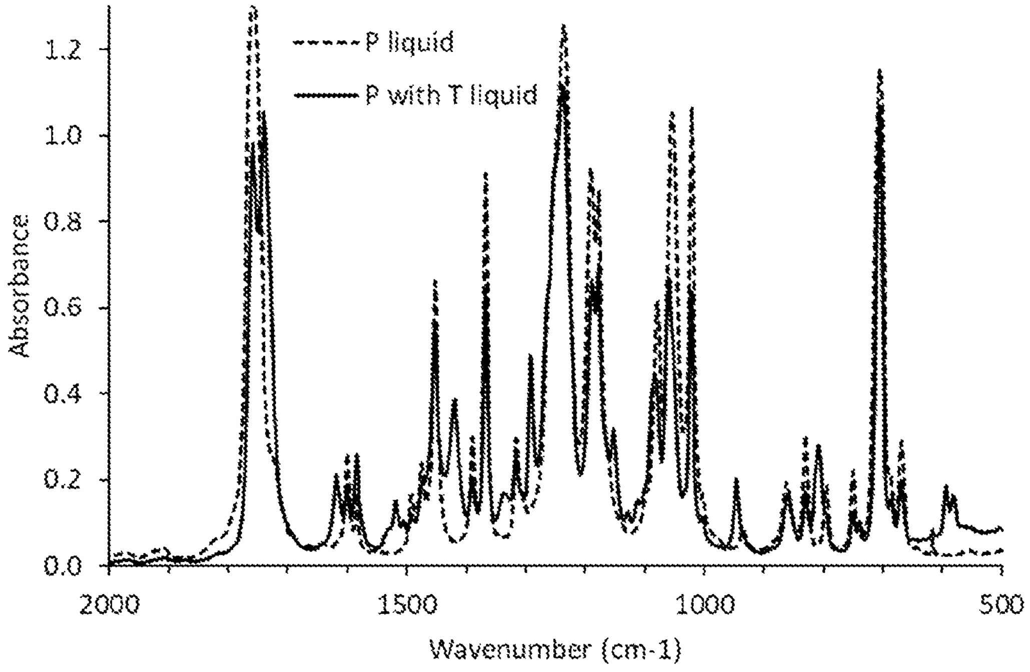
FIG. 7 is an absorbance spectrum of the embodiment of the disinfectant-containing composition from FIG. 6 as compared to the same composition without disinfectant, in which the disinfectant is thymol, and over the range of 500-2000 $cm^{-1}$

FIGS. 6 and 7 are absorbance spectra of the liquids before activation. The broken lines correspond to the smoke generating composition without thymol, and the solid lines correspond to the smoke generating composition containing thymol. The solid peak near 3500/cm provides evidence that thymol is present in the liquid. The spectral signature of thymol is presented in FIG. 5 for comparison. The concentration of thymol in this sample was approximately 30%. As expected, the sample without thymol (broken) doesn't have the characteristic peak.

Figure 8:
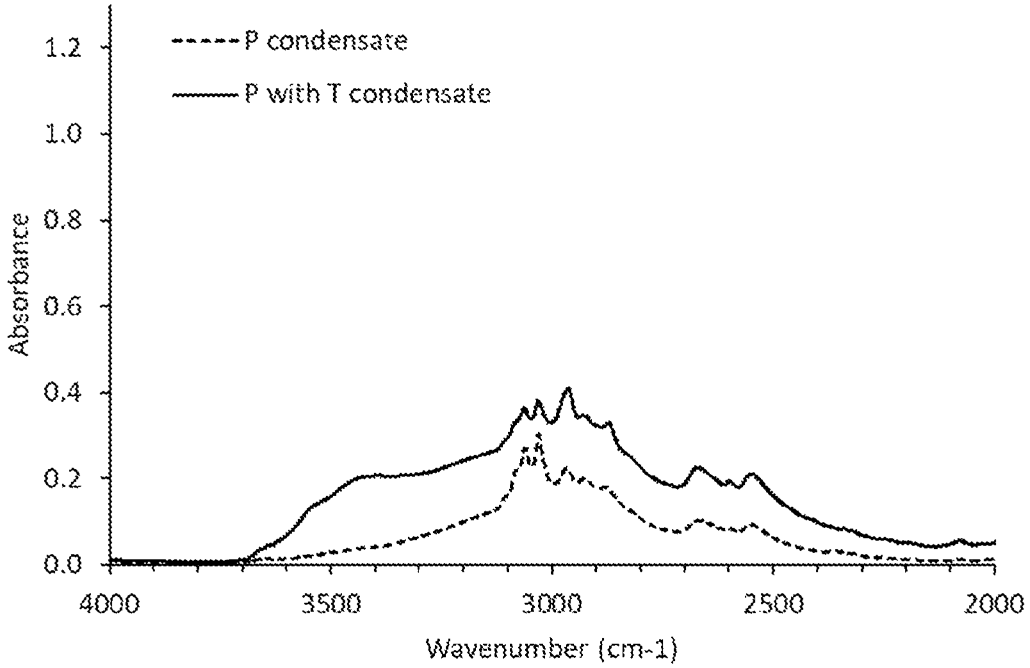
FIG. 8 is an absorbance spectrum of an embodiment of the disinfectant-containing smoke as compared to the same smoke without disinfectant, in which the disinfectant is thymol, and over the range of 2000-4000 $cm^{-1}$.
Figure 9:
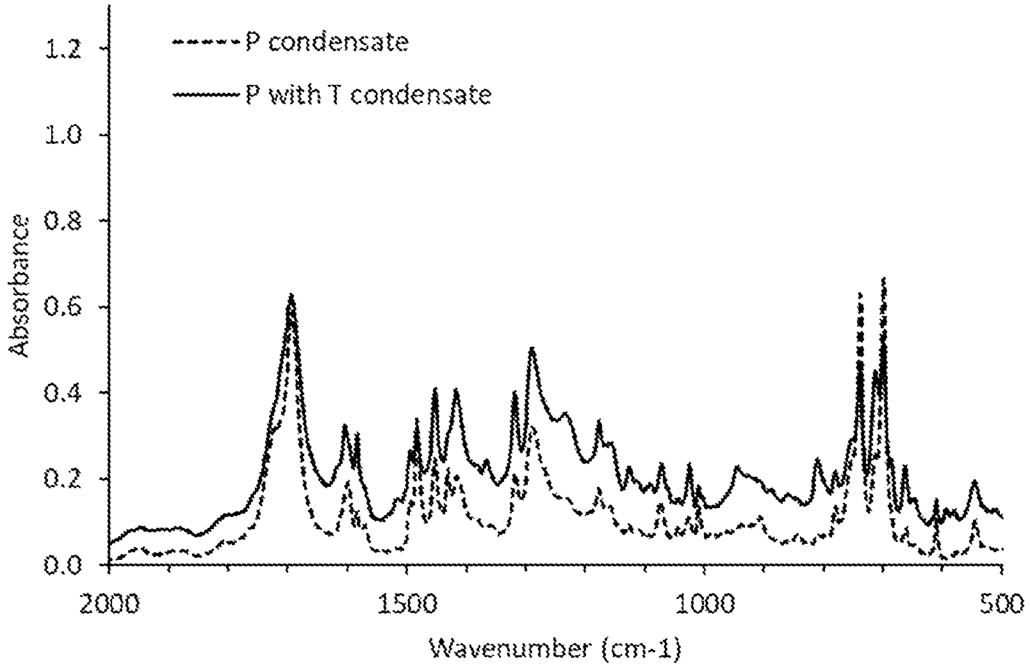
FIG. 9 is an absorbance spectrum of an embodiment of the disinfectant-containing smoke as compared to the same smoke without disinfectant, in which the disinfectant is thymol, and over the range of 500-2000 $cm^{-1}$.

FIGS. 8 and 9 show an absorbance spectrum of condensate from smoke produced from the same liquid compositions analyzed in FIGS. 6 and 7. Broken lines correspond to the spectrum of the smoke from the composition without thymol, and solid lines correspond to the spectrum of the smoke from the composition with thymol. Thymol is evident in the condensate spectra, which is evidence that the product is carried by or vaporized in the smoke. Although the signatures have broadened around 3000/cm and the peak is no longer as well defined the thymol containing condensate spectra (solid), but it is clearly more absorbing than the thymol free sample spectra (broken).

Example 3: Virucidal Activity Testing

This study was not performed under EPA Good Laboratory Practice Regulations (40 CFR Part 160). Test parameters were as follows:

TABLE 1

VIRUCIDAL ACTIVITY TEST PARAMETERS

| | |
|---|---|
| Dilution: | Ready to use (RTU) WI-38 (human lung) cells |
| Virus: | Human Coronavirus, ATCC VR-740, Strain 229E |
| Exposure Time: | 30 minutes |
| Exposure Temperature: | Room temperature (20.23 °C) |
| Exposure Humidity: | 52.57% |
| Organic Soil Load: | 1% fetal bovine serum |
| Test Medium: | Minimum Essential Medium (MEM) supplemented with 2% (v/v) heat-inactivated fetal bovine serum, 100 units/ml penicillin, 10 Lg/ml gentamicin, and 2.5 Lg/ml amphotericin B |
| Indicator Cell Cultures: | WI-38 (human lung) cells |

Preparation of Virus Films

Films of virus were prepared by spreading 200 μl of virus inoculum uniformly over the bottom of the appropriate number of 100×15 mm sterile glass petri dishes (without touching the sides of the petri dish). The virus was air-dried at 20.0° C. and 50% relative humidity until visibly dry (20 minutes).

Test Method

Input Virus Control

On the day of testing, the stock virus utilized in the assay was titered by 10-fold serial dilution and assayed for infectivity to determine the starting titer of the virus. The results of this control are for informational purposes only.

Treatment of Virus Films with the Test Substance

Prior to testing, a supplied shelf was installed into the center of the desiccator box. For each concentration of test substance assayed, the appropriate number of dried virus films were individually exposed, on the shelf inside the desiccator box located inside a fume hood, to a 1.5 g sample of test substance that was added onto the coiled end of the initiator. The initiator was placed on the interior base of the desiccator box, directly under the petri dish. The end wires of the initiator strip were connected to the clips in the box. The door to the desiccator box was tightly closed. The bare outside ends of the wires located outside of the desiccator box were touched to the two terminals of a 9 volt battery. The reaction started within in a few seconds. The plates were held uncovered for the exposure time of 30 minutes at room temperature (20.23° C.) and a relative humidity of 52.57%. Immediately following the exposure time, the plates were removed from the desiccator chamber, a 2.0 ml aliquot of test medium added and then individually scraped with a cell scraper to resuspend the contents. The contents were collected and then titered by serial dilution and assayed for infectivity and/or cytotoxicity. One replicate per batch was performed.

Treatment of Initial Dried Virus Control Film

The appropriate number of virus films were prepared as described previously. The initial virus control films were run in parallel to the test virus. Immediately after carriers were dried, a 2.0 ml aliquot of test medium is added and then individually scraped with a cell scraper to resuspend the contents. The contents were collected and then titered by serial dilution and assayed for infectivity. Three replicates were performed.

Treatment of Dried Virus Control Film

The appropriate number of virus films were prepared as described previously. The virus control films were run in parallel to the test virus and were held covered and exposed for the same exposure time and at the same exposure temperature as the test films were exposed to the test substance. Immediately following the exposure time, a 2.0 ml aliquot of test medium was added and then individually scraped with a cell scraper to resuspend the contents. The contents were collected and then titered by serial dilution and assayed for infectivity. Three replicates were performed.

Cytotoxicity Control

For each concentration of test substance assayed, the appropriate number of sterile plates were individually exposed, inside the desiccator box located inside a fume hood, to a 1.5 g sample of test substance that is added onto the coiled end of the initiators. The initiator was placed on the interior base of the desiccator box, directly under the petri dish. The end wires of the initiator strip were connected to the clips in the box. The door to the desiccator box was tightly closed. The bare outside ends of the wires located outside of the desiccator box were touched to the two terminals of a 9 volt battery. The reaction started in a few seconds. The plates were held uncovered for the exposure time. Immediately following the exposure time, the plates were removed from the desiccator chamber, a 2.0 ml aliquot of test medium was added and then individually scraped with a cell scraper to resuspend the contents. The contents were collected and then titered by serial dilution and assayed for cytotoxicity.

Assay of Non-Virucidal Level of Test Substance (Neutralization Control)

Each dilution of the neutralized test substance (cytotoxicity control dilutions) were challenged with an aliquot of low titer stock virus to determine the dilution(s) of test substance at which virucidal activity, if any, is retained. Dilutions that show virucidal activity will not be considered in determining reduction of the virus by the test substance.

Using the cytotoxicity control dilutions prepared above, an additional set of indicator cell cultures were inoculated with a 100 μL aliquot of each dilution in quadruplicate. A 100 μL aliquot of low titer stock virus was inoculated into each cell culture well and the indicator cell cultures will be incubated along with the test and virus control plates.

TABLE 2

Input Virus Control and Initial Dried Virus Control

| Dilution | Input Virus Control | Dried Virus Control Replicate #1 | Dried Virus Control Replicate #2 | Dried Virus Control Replicate #3 |
|---|---|---|---|---|
| Cell Control | 00 | 0000 | 0000 | 0000 |
| 10-1 | ++ | ++++ | ++++ | ++++ |
| 10-2 | ++ | ++++ | ++++ | ++++ |
| 10-3 | ++ | ++++ | ++++ | ++++ |
| 10-4 | ++ | ++0+ | ++0+ | +++0 |
| 10-5 | ++ | +00+ | 000+ | +000 |
| 10-6 | 00 | 0000 | 0000 | 0000 |
| 10-7 | 00 | NT | NT | NT |
| TCID50/100 μL | 105.50 | 104.75 | 104.50 | 104.50 |
| TCID50/carrier | NA | 105.05 | 104.80 | 104.80 |
| Average TCID50/100 μL | NA | | 104.60 | |
| Average TCID50/carrier | NA | | 104.90 | |

(+) = Positive for the presence of test virus;
(0) = No test virus recovered and/or no cytotoxicity present;
(NT) = Not tested;
(NA) = Not applicable.

TABLE 3

Dried Virus Control for 30 Minute Exposure Time

| Dilution | Dried Virus Control Replicate #1 | Dried Virus Control Replicate #2 | Dried Virus Control Replicate #3 |
|---|---|---|---|
| Cell Control | 0000 | 0000 | 0000 |
| $10^{-1}$ | ++++ | ++++ | ++++ |
| $10^{-2}$ | ++++ | ++++ | ++++ |
| $10^{-3}$ | ++++ | ++++ | ++++ |
| $10^{-4}$ | +++0 | +++0 | ++++ |
| $10^{-5}$ | +000 | 000+ | 0000 |
| $10^{-6}$ | 0000 | 0000 | 0000 |
| TCID50/100 μL | 104.50 | 104.50 | 104.50 |
| TCID50/carrier | 104.80 | 104.80 | 104.80 |
| Average TCID50/100 μL | | 104.50 | |
| Average TCID50/carrier | | 104.80 | |

(+) = Positive for the presence of test virus;
(0) = No test virus recovered and/or no cytotoxicity present.

TABLE 4

Effects of CleanSmoke 600 pph with 15% Thymol, 5% Thymol and 0% Thymol Following a 30 Minute Exposure to Human Coronavirus Dried on an Inanimate Surface

| Dilution | Human Coronavirus + Smoke Composition 600 pph with 15% Thymol | Human Coronavirus + Smoke Composition 600 pph with 5% Thymol | Human Coronavirus + Smoke Composition 600 pph with 0% Thymol |
|---|---|---|---|
| Cell Control | 0000 | 0000 | 0000 |
| $10^{-1}$ | TTTT | TTTT | TTTT |
| $10^{-2}$ | 0000 | 000+ | 0000 |
| $10^{-3}$ | 0000 | 0000 | 0000 |
| $10^{-4}$ | 0000 | 0000 | 0000 |
| $10^{-5}$ | 0000 | 0000 | 0000 |
| $10^{-6}$ | 0000 | 0000 | 0000 |
| TCI050/100 μL | 101.50 | 101.75 | 101.50 |
| TCI050/carrier | 101.50 | 102.05 | 101.80 |
| Log-10 Reduction per volume and carrier* | $\geq 3.10 LOG_{10}$ | $2.85 LOG_{10}$ | $\geq 3.10 LOG_{10}$ |
| Log-10 Reduction per volume and carrier** | $\geq 3.00 LOG_{10}$ | $2.75 LOG_{10}$ | $\geq 3.10 LOG_{10}$ |

(+) = Positive for the presence of test virus;
(0) = No test virus recovered and/or no cytotoxicity present;
(T) = Cytotoxicity present;
*Calculated from the initial dried virus control;
**Calculated from the 30 minute dried virus control.

TABLE 5

Cytotoxicity of CleanSmoke 600 pph with 15% Thymol, 5% Thymol and 0% Thymol on WI-38 Cell Cultures

| Dilution | Cytotoxicity Control with 15% Thymol | Cytotoxicity Control with 5% Thymol | Cytotoxicity Control with 0% Thymol |
|---|---|---|---|
| Cell Control | 0000 | 0000 | 0000 |
| $10^{-1}$ | TTTT | TTTT | TTTT |
| $10^{-2}$ | 0000 | 0000 | 0000 |
| $10^{-3}$ | 0000 | 0000 | 0000 |
| $10^{-4}$ | 0000 | 0000 | 0000 |
| $10^{-5}$ | 0000 | 0000 | 0000 |
| $10^{-6}$ | 0000 | 0000 | 0000 |
| TCD50/100 μL | 101.50 | 101.50 | 101.50 |

(0) = No test virus recovered and/or no cytotoxicity present;
(T) = Cytotoxicity present.

TABLE 6

Non-Virucidal Level of Test Substance (Neutralization Control)

| Dilution | Test Virus+ Cytotoxicity Control with 15% Thymol | Test Virus+ Cytotoxicity Control with 5% Thymol | Test Virus+ Cytotoxicity Control with 0% Thymol |
|---|---|---|---|
| Cell Control | 0000 | 0000 | 0000 |
| $10^{-1}$ | TTTT | TTTT | TTTT |
| $10^{-2}$ | ++++ | ++++ | ++++ |
| $10^{-3}$ | ++++ | ++++ | ++++ |
| $10^{-4}$ | ++++ | ++++ | ++++ |
| $10^{-5}$ | ++++ | ++++ | ++++ |
| $10^{-6}$ | ++++ | ++++ | ++++ |

(+) = Positive for the presence of test virus after low titer stock virus added (neutralization control);
(0) = No test virus recovered and/or no cytotoxicity present;
(T) = Cytotoxicity present.

Example 4: Antibacterial Testing

Tests were conducted smoke composition, smoke composition with varied % thymol, varied weight of smoke composition at a fixed % and disinfecting dwell time for a fixed smoke composition formulation. Each bacterium had to be grown, exposed, and then analyzed. Specifically, the Gram-positive bacterium used was *Staphylococcus aureus* and the Gram-negative bacterium analyzed was *Enterobacter aerogenes*. The data below survival rates for smoke composition with and without thymol for a 15 and 30 exposure time, and 1.2, 1.35 grams and 2.4 grams of base material.

The results show 99.9% effectiveness in multiple situations, as discussed below.

The bacteriological efficacy results presented in this section show mixture B as a 50-50 wt % mixture of Luperox P and Luperox 231. Luperox P is able to dissolve significant amount of thymol, we have found that we can dissolve up to 45% (wt./wt. %) thymol in Luperox P. We have confirmed through FTIR analysis of the resulting mist that thymol is carried up into the mist in relation to its proportion in the base material. This result is shown in FIGS. 13A-C which is the FTIR spectrum of Luperox P produced mist along with dissolved thymol for several different thymol concentrations. The main thymol peaks are at 920 $cm^{-1}$ and 1142 $cm^{-1}$, the other IR peaks correspond to the Luperox P obscurant. The spectra show that thymol is carried into the mist as a component of the obscurant producing reaction.

Bacteriological efficacy testing closely followed ASTM testing standards. The efficacy of a gram-positive (*S. aureus*) and gram-negative (*E. aerogenes*) strains was determined. Testing was conducted in a desiccator/dry box. Three different samples of each bacteria were used for each test. Testing was done with a set amount of base material, with or without thymol, leading to approximately constant amounts of Luperox mist and varying amounts of dissolved thymol. Dissolved thymol concentrations varied between 5-40 wt % thymol in Luperox. Since the base material is composed of three components (Luperox, monomer, fumed silica), minus thymol, the actual mist mass in the chamber is approximately 80% of the total base material mass, approximately 0.95 grams of Luperox mist per cu. ft. After exposure the bacteria were incubated for 24-48 under specified temperature control. Efficacy results were reported in terms of the mass of the starting base material, the amount of thymol dissolved in the base material, and the time (15 or 30 minutes) the bacteria were exposed to the mist.

The specified incubation period the number of surviving bacterial colonies were counted. Table 7 shows the raw results from a test for *Staphylococcus aureus*. The exposure was for 15 minutes with 1.2 grams of starting material. Smoke only, smoke with 5% thymol, and smoke with 15% thymol were tested for efficacy. The raw data in the table contain the negative control values, the positive (no exposure) control values and then the bacteria count values for the various tests. The solutions were diluted several times until the number of colonies were able to be counted. Four separate gram-positive and gram-positive efficacy tests were performed.

The raw EMSL efficacy results were then reduced and analyzed to produce overall efficacy results. The overall efficacy results are show in Tables 8a-d, and 9a-d. Table 7 shows the number of colonies for each of the three bacteria sample for each test. The average and standard deviation were taken for each dilution and data set were three separate counts were given; data sets that did not have three independent count values were not included in the analysis. Table 7 shows an example where EMSL was able to obtain bacteria counts at dilutions lower than the dilutions required to count the positive controls; indicating a disinfectant action of the mist. In cases where disinfecting action was seen at lower dilutions than the positive control extrapolated positive control values were used to calculate the efficacy of an individual expose efficacy tests. The bacteria count analysis at 107 dilution are not included in Tables 8 and 9 since the count rates are so low that they are probably not statistically valid. In Table 7 T1=Smoke only, T2=Smoke+5%, T3=Smoke+15% (2.4 grams/treatment), 15 minutes exposure.

Table 8a-d shows the efficacy results for the four test groups conducted on *S. aureus* (gram-positive) bacteria. The four tests are a) 1.2 grams of base material (approximately 0.96 grams of mist) with 0%, 5%, and 15% dissolved thymol, with a 15 minute expose; b) 2.4 grams of base material (approximately 1.92 grams of mist) with 0%, 5%, and 15% thymol with a 15 minute exposure; c) 1.35 grams of base material (0.96 grams of mist) with 30% and 40% thymol; and d) 1.2 grams of base material with 0%, 5%, 15%, and 30% thymol with a 30 minute exposure, and Luperox P/Luperox 231 base mixture with 15% and 30% thymol in Luperox P for a 30 minute exposure.

The first efficacy test with 1.2 grams of base material, 15 minute exposure, and 0, 5, and 15% thymol are the base data for analysis. Exposure to the mist without thymol resulted in about an 80% efficacy. The addition of 5% thymol increases the efficacy to 97%, while increasing the thymol concentration to 15% results in almost no additional efficacy. Table 8b shows the efficacy results with a doubling of the base material while holding the exposure time to 15 minutes. 99.9% efficacy was achieved with the mist only. The mist with 5% thymol achieved 94% efficacy while the 15% thymol most only achieved 84% efficacy. Without wishing to be bound by any hypothesis, it is possible that the thymol may not be in a form where it is the most effective. Table 8c shows the results for 30% and 40% thymol with approximately 0.96 grams of mist for 15 minute exposure. The 40% thymol mist achieved 99% efficacy; however, the 30% thymol results are less than would be expected based on the 5 and 15% results and again lead us to believe that the thymol is not working to its potential effectiveness. The final set of gram-positive bacteria tests are presented in Table 8d where approximately of 0.96 grams of mist were used for 30 minutes of exposure. The efficacy rates for the 0% thymol mist are lower than for a 15 minute exposure. 5, 15, and 30% thymol mist have efficacy rates between 94 and 84%, however, there is no linear efficacy rate with thymol concentration and the efficacy rate are slightly lower than for a 15 minute exposure. The efficacy rates are the mixed (Luperox P/Luperox 231) CoolSmoke®/CleanSmoke® mist are lower than for just Luperox P mist. However, this is not unexpected since there is a lower concentration of Luperox P in the mist and this test was directed to improving the efficacy of gram-negative bacteria. Table 2a shows analyzed data for *S. aureus* exposed to 1.2 grams of base material with 0%, 5%, and 15% thymol, smoke exposure for 15 minutes. This CoolSmoke formulation achieved the 97-98% efficacy.

Table 8b shows analyzed Data for *S. aureus* exposed to 2.4 grams of base material with 0%, 5%, and 15% thymol, smoke exposure for 15 minutes. This CoolSmoke® formulation achieved the 99-99.9% efficacy.

Table 8c shows analyzed data for *S. aureus* exposed to 1.35 grams of base material with 30%, and 40% thymol, smoke exposure for 15 minutes. This CoolSmoke® formulation achieved the 99% efficacy.

Table 8d shows analyzed Data for *S. aureus* exposed to 1.2 grams of base material with 0%, 5%, 15% and 30% thymol, smoke exposure for 15 minutes and for CoolSmokeB (50-50 Luperox P and Luperox 231) with 0%, 15% and 30% thymol in the Luperox P component, exposure for 15 minutes. This test achieved a 94% efficacy.

Tables 9a-d are similar analysis with the same tests for the gram-negative bacteria *E. aerogenes*. Lower efficacy rates were seen for *E. aerogenes* than for *S. aureus*. Table 9a shows that there is a limited efficacy of 0%, 5%, and 15% thymol on *E. aerogenes* from a 15 minutes exposure with 1.2 grams of base material. Increasing the base material mass to 2.4 grams results in a 98% efficacy for the mist without thymol, the addition of thymol leads to a decrease in the efficacy. A further increase of the thymol concentration to 30 and 40% does not increase the efficacy, Table 9c. The analysis of the results in Table 9d shows that increasing the exposure time, or the addition of Luperox 231 to the mist does not increase the overall efficacy. Table 9a shows analyzed data for *E. aerogenes* exposed to 1.2 grams of base material with 0%, 5%, and 15% thymol, smoke exposure for 15 minutes. This CoolSmoke formulation achieved the 79% efficacy.

Table 9b shows analyzed data for *E. aerogenes* exposed to 2.4 grams of base material with 0%, 5%, and 15% thymol, smoke exposure for 15 minutes. This CoolSmoke® formulation achieved the 98% efficacy.

Table 9c shows analyzed data for *E. aerogenes* exposed to 1.35 grams of base material with 30%, and 40% thymol, smoke exposure for 15 minutes. This CoolSmoke® formulation achieved the 85% efficacy.

Table 8d shows analyzed data for *E. aerogenes* exposed to 1.2 grams of base material with 0%, 5%, 15% and 30% thymol, smoke exposure for 15 minutes and for CoolSmokeB (50-50 Luperox P and Luperox 231) with 0%, 15% and 30% thymol in the Luperox P component, exposure for 15 minutes. This test achieved a 79% efficacy. The formulation of CleanSmokeB is not identical to the CleanSmoke.

Several of the bacteriological tests, particularly with *S. aureus*, yielded efficacy rates of 99 or 99.9%. Lower efficacy results were obtained with gram-negative *E. aerogenes*. However, in many of our results there seems to be lacking a linear response to either the CoolSmoke® mist itself or to the addition of thymol; this can be seen in comparing the data in Tables 8a and 8c. While we have 98% efficacy with 1.2 grams of material with 15% thymol in Table 8a, increasing the thymol concentration, Table 8c, to 30% does not increase the efficacy rates. Without wishing to be bound by any hypothesis, this may be due to the fact that while increasing the thymol concentration in the mist, the thymol is not in an active form where it can kill the bacteria. This may be due to the pKa of the Luperox P-thymol being too high.

The combination of Luperox P and Luperox 231 CleanSmoke® did not substantially increase the efficacy of gram-negative bacteria.

CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

TABLE 7

| | Raw Data - EMSL 292006376 *Staphylococcus aureus* (ATCC 6538); Raw Counts | | | | | | | | | | | | | | |
|---|---|---|---|---|---|---|---|---|---|---|---|---|---|---|---|
| Dilution | N1 | N2 | N3 | P1 | P2 | P3 | T1.1 | T1.2 | T1.3 | T2.1 | T2.2 | T2.3 | T3.1 | T3.2 | T3.3 |
| 10^1 | | | | ND | ND | ND | ND | ND | ND | ND | ND | ND | ND | ND | ND |
| 10^2 | ND | ND | ND | TNTC | TNTC | TNTC | 7 | 153 | 36 | TNTC | TNTC | TNTC | TNTC | TNTC | 272 |
| 10^3 | ND | ND | ND | TNTC | TNTC | TNTC | 0 | 21 | 2 | 133 | TNTC | 211 | 44 | TNTC | 23 |
| 10^4 | ND | ND | ND | 110 | 40 | 246 | 0 | 2 | 0 | 9 | 33 | 18 | 5 | 88 | 1 |
| 10^5 | ND | ND | ND | 15 | 5 | 42 | 0 | 0 | 0 | 0 | 3 | 1 | 1 | 8 | 1 |
| 10^6 | ND | ND | ND | 1 | 0 | 5 | 0 | 0 | 0 | 0 | 0 | 0 | 0 | 1 | 0 |
| 10^7 | ND | ND | ND | 0 | 0 | 5 | 0 | 0 | 0 | 0 | 0 | 0 | 0 | 0 | 0 |

TABLE 8a

292005574 Sa Gram-positive Analyzed Data *Staphylococcus aureus* (ATCC 6538)
Survival Rates CoolSmoke/CleanSmoke 15 minute exposure, 1.2 grams base material

| | Positive Control | | T1 CoolSmoke | | | | T2 CleanSmoke 5% Thymol | | | | T3 CleanSmoke 15% Thymol | | | |
|---|---|---|---|---|---|---|---|---|---|---|---|---|---|---|
| Dilution | ave | std | ave | std | survive | kill % | ave | std | survive | kill % | ave | std | survive | kill % |
| 10^2 | | | | | | | | | | | | | | |
| 10^3 | | | | | | | 102.67 | 109.20 | 0.04 | 98% | 55.33 | 17.01 | 0.02 | 98% |
| 10^4 | 229.67 | 68.24 | 49.67 | 28.57 | 0.22 | 78% | 6.00 | 7.21 | 0.03 | 97% | 6.33 | 1.53 | 0.03 | 97% |
| 10^5 | 24.00 | 6.08 | 4.67 | 2.08 | 0.19 | 81% | 1.00 | 1.73 | 0.04 | 96% | 0 | 0 | 0 | 100% |
| 10^6 | 3.67 | 0.58 | 1.67 | 2.08 | 0.45 | 55% | 0 | 0 | 0 | 100% | 0 | 0 | 0 | 100% |

TABLE 8b

292006376 Sa Gram-positive Analyzed Data *Staphylococcus aureus* (ATCC 6538)
Survival Rates CoolSmoke/CleanSmoke, 2.4 grams of base material, 15 minute exposure

| | Positive Control | | T1 CoolSmoke | | | | T2 CleanSmoke 5% Thymol | | | | T3 CleanSmoke 15% Thymol | | | |
|---|---|---|---|---|---|---|---|---|---|---|---|---|---|---|
| Dilution | ave | std | ave | std | survive | kill % | ave | std | survive | kill % | ave | std | survive | kill % |
| 10^2 | | | 65.33 | 77.29 | 0.00 | 100 | | | | | | | | |
| 10^3 | | | 7.67 | 11.59 | 0.01 | 99 | | | | | | | | |
| 10^4 | 132.00 | 104.75 | 0.67 | 1.15 | 0.01 | 99 | 20.00 | 12.12 | 0.15 | 85% | 31.33 | 49.12 | 0.24 | 76% |
| 10^5 | 20.67 | 19.14 | 0 | 0 | 0 | 100 | 1.33 | 1.63 | 0.06 | 94% | 3.33 | 4.04 | 0.16 | 84% |
| 10^6 | 2.00 | 2.65 | 0 | 0 | 0 | 100 | 0 | 0 | 0 | 100% | 0.33 | 0.58 | 0.17 | 83% |

TABLE 8c

292006554 Sa Gram-positive Analyzed Data *Staphylococcus aureus* (ATCC 6538)
Survival Rates CoolSmoke/CleanSmoke, 1.35 grams base material, 15 minute exposure

| | Positive Control | | T1 CoolSmoke 30% Thymol | | | | T2 CleanSmoke 40% Thymol | | | |
|---|---|---|---|---|---|---|---|---|---|---|
| Dilution | ave | std | ave | std | survive | kill % | ave | std | survive | kill % |
| 10^2 | | | | | | | | | | |
| 10^3 | | | | | | | 31.67 | 13.65 | 0.01 | 99% |
| 10^4 | | | 28.67 | 23.71 | 0.13 | 87% | 2.67 | 2.52 | 0.01 | 99% |
| 10^5 | 21.33 | 17.01 | 3.00 | 4.36 | 0.14 | 86% | 0.67 | 1.15 | 0.03 | 97% |
| 10^6 | 2.00 | 2.65 | 0.33 | 0.58 | 0.17 | 83% | 0.00 | 0.00 | 0.00 | 100% |

TABLE 8d

292006983 Sa Gram-positive Analyzed Data *Staphylococcus aureus* (ATCC 6538) Survival Rates CoolSmoke/Clean Smoke 30 exposure time

| | Positive Control | | T1 CoolSmcke @ 1.2 gms | | | | T2 CleanSmoke 5% Thymol @ 1.2 gms | | | |
|---|---|---|---|---|---|---|---|---|---|---|
| Dilution | ave | std | ave | std | survive | kill % | ave | std | survive | kill % |
| 10^2 | | | | | | | | | | |
| 10^3 | | | | | | | | | | |
| 10^4 | | | | | | | 104.33 | 168.60 | 0.13 | 87 |
| 10^5 | 78.33 | 29.26 | 52.0 | 27.22 | 0.66 | 34 | 7.67 | 11.59 | 0.10 | 90 |
| 10^6 | 10.33 | 5.86 | 4.0 | 3.00 | 0.39 | 61 | 1.00 | 1.73 | 0.10 | 90 |

| | T3 Clean Smoke 15% Thymol @ 1.2 gms | | | | 74 -CleanSmoke 30% Thymol @ 1.2 gms | | | |
|---|---|---|---|---|---|---|---|---|
| Dilution | ave | std | survive | kill % | ave | std | survive | kill % |
| 10^2 | | | | | | | | |
| 10^3 | | | | | | | | |
| 10^4 | 16.67 | 25.40 | 0.21 | 79 | 134.67 | 28.15 | 0.17 | 83 |
| 10^5 | 1.67 | 2.89 | 0.16 | 84 | 10.67 | 1.15 | 0.14 | 86 |
| 10^6 | | | | | 0.67 | 0.58 | 0.06 | 94 |

| | Positive Control | | T5 CoclSmokeB @ 1.2 gms | | | | 16 CleanSmokeB 7.5% Thymol @ 1.2 gms | | | |
|---|---|---|---|---|---|---|---|---|---|---|
| Dilution | ave | std | ave | std | survive | kill % | ave | std | survive | kill % |
| 10^2 | | | | | | | | | | |
| 10^3 | | | | | | | | | | |
| 10^4 | | | | | | | | | | |
| 10^5 | 78.33 | 29.26 | 31.67 | 13.65 | 0.40 | 60 | 43.67 | 7.64 | 0.56 | 44 |
| 10^6 | 10.33 | 5.86 | 2.67 | 2.31 | 0.26 | 74 | 5.00 | 7.00 | 0.48 | 52 |

| | T7 CleanSmokeB 15%Thymol@1.2gms | | | |
|---|---|---|---|---|
| Dilution | ave | std | survive | kill % |
| 10^2 | | | | |
| 10^3 | | | | |
| 10^4 | | | | |
| 10^5 | 48.33 | 8.39 | 0.62 | 38 |
| 10^6 | 2.33 | 1.53 | 0.23 | 77 |

TABLE 9a

29200574 Ea Gram-negative Analyzed *Enterobacter aerogenes* (ATCC 13048) Survival Rates CoolSmoke/CleanSmoke 15 min exposure time

| | Positive Control | | T1 CoolSmoke | | | | T2 CleanSmoke 5% Thymol | | | | T3 CleanSmoke 15% Thymol | | | |
|---|---|---|---|---|---|---|---|---|---|---|---|---|---|---|
| Dilution | ave | std | ave | std | survive | % kill | ave | std | survive | % kill | ave | std | survive | % kill |
| 10^2 | | | | | | | | | | | | | | |
| 10^3 | | | | | | | | | | | | | | |
| 10^4 | | | | | | | | | | | | | | |
| 10^5 | 150.0 | 59.3 | 51.33 | 13.01 | 0.34 | 66% | 32.00 | 16.09 | 0.21 | 79% | 48.33 | 4.16 | 0.32 | 68 |
| 10^6 | 11.67 | 7.02 | 5.00 | 4.36 | 0.43 | 57% | 3.69 | 3.5 | 0.31 | 69% | 7.33 | 5.13 | 0.63 | 37 |

TABLE 9b

292005574 Ea Gram-negative Analyzed *Enterobacter aerogenes* (ATCC 13048) Survival Rates CoolSmoke/CleanSmoke 15 minute exposure

| | Positive Control | | T1 CoolSmoke @ 2.4 gms, | | | | T2 CleanSmoke 5% Thymol @ 2.4 gms, | | | | T3 CleanSmoke 15% Thymol @ 2.4 gms, | | | |
|---|---|---|---|---|---|---|---|---|---|---|---|---|---|---|
| Dilution | ave | std | ave | std | survive | % kill | ave | std | survive | % kill | ave | std | survive | % kill |
| 10^2 | | | | | | | | | | | | | | |
| 10^3 | | | | | | | | | | | | | | |
| 10^4 | | | 45.00 | 45.92 | 0.02 | 98 | | | | | | | | |
| 10^5 | 251.33 | 259.15 | 4.67 | 6.43 | 0.02 | 98 | 40.00 | 21.07 | 0.16 | 84 | 40.00 | 21.07 | 0.16 | 84 |
| 10^6 | 27.67 | 23.76 | 0 | 0 | 0 | 100 | 4.00 | 1.73 | 0.14 | 86 | 4.00 | 1.73 | 0.14 | 86 |

TABLE 9c

292006554 Ea Gram-negative Analyzed *Enterobacter aerogenes* (ATCC 13048) Survival Rates CoolSmoke/CleanSmoke 1.35 grams of base material, 15 minutes exposure

| | Positive Control | | T1 CoolSmoke 30% Thymol | | | | T2 CleanSmoke 40% Thymol | | | |
|---|---|---|---|---|---|---|---|---|---|---|
| Dilution | ave | std | ave | std | survive | % kill | ave | std | survive | Kill % |
| 10^2 | | | | | | | | | | |
| 10^3 | | | | | | | | | | |
| 10^4 | | | | | | | | | | |
| 10^5 | 125.33 | 10.69 | 54.33 | 21.13 | 0.43 | 57% | 22.33 | 14.09 | 0.18 | 82 |
| 10^6 | 11.00 | 5.57 | 6.67 | 2.08 | 0.61 | 39% | 1.67 | 1.17 | 0.15 | 85 |

TABLE 9d

292006983 Ea Gram-negative Analyzed Enterobacter sercgenes (ATCC 13048) Survival Rates CoolSmoke/CleanSmoke 1.2 gams base material, 30 exposure time

| | Positive Control | | T1 CoolSmoke | | | | T2 CleanSmoke 5% Thymol | | | |
|---|---|---|---|---|---|---|---|---|---|---|
| Dilution | ave | std | ave | std | survive | kill % | ave | std | survive | kill % |
| 10^2 | | | | | | | | | | |
| 10^3 | | | | | | | | | | |
| 10^4 | | | | | | | | | | |
| 10^5 | 199.00 | 37.75 | 150.00 | 39.84 | 0.75 | 25 | 47.0 | 9.54 | 0.24 | 76 |
| 10^6 | 19.33 | 6.03 | 18.67 | 15.57 | 0.97 | | 4.0 | 4.00 | 0.21 | 79 |

| | Positive Control | | T3 Clean Smoke 15% Thymol | | | | T4 -CleanSmoke 30% Thymol | | | |
|---|---|---|---|---|---|---|---|---|---|---|
| Dilution | ave | std | ave | std | survive | kill % | ave | std | survive | kill % |
| 10^2 | | | | | | | | | | |
| 10^3 | | | | | | | | | | |
| 10^4 | | | | | | | | | | |
| 10^5 | 258.67 | 41.97 | 51.0 | 19.05 | 0.2 | 80 | 0.80 | 9.54 | 0.24 | 76 |
| 10^6 | 24.33 | 7.02 | 2.33 | 0.58 | 0.1 | 90 | 0.90 | 4.00 | 0.21 | 79 |

| | Positive Control | | T5 CcolSmokeB | | | | T6 CleanSmokeB 15% Thymol | | | | T7 CleanSmokeB 30% Thymol | | | |
|---|---|---|---|---|---|---|---|---|---|---|---|---|---|---|
| Dilution | ave | std | ave | std | survive | kill % | ave | std | survive | kill % | ave | std | survive | kill % |
| 10^2 | | | | | | | | | | | | | | |
| 10^3 | | | | | | | | | | | | | | |
| 10^4 | | | | | | | | | | | | | | |
| 10^5 | 109.17 | 37.75 | 133.00 | 6.56 | 1.22 | -22 | 77.67 | 47.35 | 0.71 | 29 | 64.33 | 27.05 | 0.59 | 41 |
| 10^6 | 9.83 | 6.03 | 12.33 | 8.33 | 1.25 | -25 | 8.00 | 6.08 | 0.81 | 19 | 4.00 | 2.00 | 0.41 | 59 |

The following is claimed:

1. A non-pyrotechnic method of generating disinfectant-containing smoke, comprising initiating a frontal polymerization reaction in a composition for the non-pyrotechnic generation of disinfectant-containing smoke, and generating smoke comprising thymol in an amount effective to kill or inactivate at least 90% of a bacterium according to ASTM E1153-14.

2. The method of claim 1, wherein the composition for the non-pyrotechnic generation of disinfectant-containing smoke comprises an initiator compound and thymol in an amount effective to kill or inactivate at least 90% of a bacterium according to ASTM E1153-14.

3. The method of claim 1, wherein the composition for the non-pyrotechnic generation of disinfectant-containing smoke comprises fumed silica.

4. The method of claim 1, wherein the composition for the non-pyrotechnic generation of disinfectant-containing smoke comprises an organic peroxide as the initiator compound.

5. The method of claim 1, wherein the composition for the non-pyrotechnic generation of disinfectant-containing smoke comprises as the initiator compound: 1,1-bis(tert-butylperoxy)-3,3,5-trimethylcyclohexane, di-tert-butyl peroxide, tert-butyl peroxybenzoate, tert-butyl hydroperoxide, cyclohexyl hydroperoxide, or a combination of two or more of the foregoing.

6. The method of claim 1, wherein the composition for the non-pyrotechnic generation of disinfectant-containing smoke comprises tert-butyl peroxybenzoate as the initiator compound.

7. The method of claim 1, wherein the composition for the non-pyrotechnic generation of disinfectant-containing smoke comprises a filler in an amount effective to propagate the frontal polymerization reaction.

8. The method of claim 1, wherein the composition for the non-pyrotechnic generation of disinfectant-containing smoke comprises a filler at a concentration of at least 5% w/w.

9. The method of claim 1, wherein the composition for the non-pyrotechnic generation of disinfectant-containing smoke comprises a filler at a concentration of 5-20% w/w.

10. The method of claim 1, wherein the composition for the non-pyrotechnic generation of disinfectant-containing smoke comprises a fumed silica filler at a concentration of 5-20% w/w.

11. The method of claim 1, wherein the composition for the non-pyrotechnic generation of disinfectant-containing smoke comprises thymol at a mass concentration at least 1% of the mass concentration of the initiator.

12. The method of claim 1, wherein the composition for the non-pyrotechnic generation of disinfectant-containing smoke comprises thymol at a mass concentration at least 8% of the mass concentration of the initiator.

13. The method of claim 1, wherein the smoke contains an amount of thymol effective to kill or inactivate at least 90% of a virus according to ASTM E1053-20.

14. The method of claim 1, wherein the smoke contains an amount of thymol effective to kill or inactivate at least 90% of SARS-CoV-2 according to ASTM E1053-20.

15. The method of claim 1, wherein the smoke contains an amount of thymol effective to kill or inactivate at least 90% of *Staphylococcus aureus* according to ASTM E3218-19.

16. The method of claim 1, wherein the composition for the non-pyrotechnic generation of disinfectant-containing smoke comprises: tert-butyl peroxybenzoate, thymol, and fumed silica.

* * * * *